(12) United States Patent
Nagai et al.

(10) Patent No.: US 9,417,254 B2
(45) Date of Patent: Aug. 16, 2016

(54) ANALYSIS APPARATUS AND MEASUREMENT UNIT

(75) Inventors: Takaaki Nagai, Kobe (JP); Masaharu Shibata, Kobe (JP); Yuichi Hamada, Kobe (JP); Daigo Fukuma, Kobe (JP)

(73) Assignee: SYSMEX CORPORATION, Kobe-Shi, Hyogo (JP)

( * ) Notice: Subject to any disclaimer, the term of this patent is extended or adjusted under 35 U.S.C. 154(b) by 1040 days.

(21) Appl. No.: 12/875,926

(22) Filed: Sep. 3, 2010

(65) Prior Publication Data

US 2010/0332144 A1    Dec. 30, 2010

Related U.S. Application Data

(63) Continuation of application No. PCT/JP2009/054249, filed on Mar. 6, 2009.

(30) Foreign Application Priority Data

| Mar. 7, 2008 | (JP) | 2008-57382 |
| Mar. 7, 2008 | (JP) | 2008-57661 |
| Mar. 7, 2008 | (JP) | 2008-57972 |
| Mar. 7, 2008 | (JP) | 2008-58007 |
| Mar. 7, 2008 | (JP) | 2008-58302 |

(51) Int. Cl.
*G01N 33/48* (2006.01)
*G06F 15/00* (2006.01)
*G01N 35/02* (2006.01)
(Continued)

(52) U.S. Cl.
CPC .......... *G01N 35/026* (2013.01); *G01N 35/0092* (2013.01); *G01N 35/0095* (2013.01); *G01N 2035/00326* (2013.01); *G01N 2035/0412* (2013.01); *G01N 2035/0484* (2013.01); *Y10T 436/114165* (2015.01)

(58) Field of Classification Search
CPC ............ G01N 35/026; G01N 35/0092; G01N 35/0095; G01N 2035/00326; G01N 2035/0412; G01N 2035/0484; Y10T 436/114165
See application file for complete search history.

(56) References Cited

U.S. PATENT DOCUMENTS

| 5,207,986 A | * | 5/1993 | Kadota et al. | 422/65 |
| 5,209,903 A | * | 5/1993 | Kanamori et al. | 422/65 |
| 5,232,081 A | * | 8/1993 | Kanamori | 198/465.2 |

(Continued)

FOREIGN PATENT DOCUMENTS

| JP | 03-094159 A | 4/1991 |
| JP | 03-279863 A | 12/1991 |

(Continued)

OTHER PUBLICATIONS

International Search Report for International Application No. PCT/JP2009/054249, dated Mar. 31, 2009, 2 pages.

*Primary Examiner* — Jill Warden
*Assistant Examiner* — Benjamin Whatley
(74) *Attorney, Agent, or Firm* — Brinks Gilson & Lione

(57) ABSTRACT

This analysis apparatus includes a plurality of a plurality of measurement units of mutually identical types generating measurement data by measuring the specimens, a transporter transporting the specimens to the respective ones of the plurality of measurement units, a display, common to the plurality of measurement units, displaying the analytical results generated by analyzing the measurement data and a transmitter transmitting the analytical results to a host computer.

12 Claims, 20 Drawing Sheets

(51) Int. Cl.
*G01N 35/00* (2006.01)
*G01N 35/04* (2006.01)

(56) References Cited

U.S. PATENT DOCUMENTS

| | | | |
|---|---|---|---|
| 5,270,012 | A | 12/1993 | Kanamori et al. |
| 5,356,595 | A | 10/1994 | Kanamori et al. |
| 5,588,555 | A | 12/1996 | Kanamori et al. |
| 5,985,215 | A * | 11/1999 | Sakazume et al. ............. 422/67 |
| 6,019,945 | A | 2/2000 | Ohishi et al. |
| 6,444,171 | B1 | 9/2002 | Sakazume et al. |
| 6,599,749 | B1 | 7/2003 | Kodama et al. |
| 6,772,650 | B2 | 8/2004 | Ohyama et al. |
| 6,938,502 | B2 | 9/2005 | Tanoshima et al. |
| 7,283,217 | B2 | 10/2007 | Ikeuchi et al. |
| 7,450,223 | B2 | 11/2008 | Ikeuchi et al. |
| 7,597,848 | B1 * | 10/2009 | Ameling ............ G01N 35/028 422/504 |
| 7,633,604 | B2 | 12/2009 | Ikeuchi et al. |
| 7,931,862 | B2 | 4/2011 | Toyoda et al. |
| 8,556,564 | B2 * | 10/2013 | Miller ..................... 414/331.11 |
| 2003/0202905 | A1 * | 10/2003 | Devlin et al. .................. 422/64 |
| 2004/0053414 | A1 | 3/2004 | Devlin, Sr. |
| 2005/0070019 | A1 * | 3/2005 | Yamamoto ..................... 436/43 |
| 2005/0196320 | A1 * | 9/2005 | Veiner et al. .................... 422/63 |
| 2006/0029520 | A1 | 2/2006 | Tanoshima et al. |
| 2006/0216199 | A1 * | 9/2006 | Koike .............................. 422/65 |
| 2006/0265173 | A1 * | 11/2006 | Mishima et al. .............. 702/118 |
| 2007/0110617 | A1 | 5/2007 | Nagai et al. |
| 2008/0113440 | A1 * | 5/2008 | Gurney et al. .................. 436/48 |
| 2008/0190735 | A1 * | 8/2008 | Luoma ..................... B01L 9/00 198/340 |

FOREIGN PATENT DOCUMENTS

| | | |
|---|---|---|
| JP | 04-316169 A | 11/1992 |
| JP | 06-000770 Y2 | 1/1994 |
| JP | 06-201536 Y2 | 7/1994 |
| JP | 08-094768 A | 4/1996 |
| JP | 09-043248 A | 2/1997 |
| JP | 09-281113 A | 10/1997 |
| JP | 2550510 Y2 | 10/1997 |
| JP | 10-090276 A | 4/1998 |
| JP | 10-282114 A | 10/1998 |
| JP | 11-064208 A | 3/1999 |
| JP | 2000-046842 A | 2/2000 |
| JP | 2000-137621 A | 5/2000 |
| JP | 2000-314737 A | 11/2000 |
| JP | 2001-074754 A | 3/2001 |
| JP | 2002-277477 A | 9/2002 |
| JP | 2003-066050 A | 3/2003 |
| JP | 2003-083960 A | 3/2003 |
| JP | 2004-226065 A | 8/2004 |
| JP | 2005-257450 A | 9/2005 |
| JP | 2006-208286 A | 8/2006 |
| JP | 2007-139462 A | 6/2007 |
| JP | 63-085457 A | 4/2008 |

* cited by examiner

ANALYSIS APPARATUS AND MEASUREMENT UNIT

RELATED APPLICATIONS

This application is a continuation of PCT/JP2009/054249 filed on Mar. 6, 2009, which claims priority to Japanese Application Nos. 2008-057661 filed on Mar. 7, 2008, 2008-057382 filed on Mar. 7, 2008, 2008-057972 filed on Mar. 7, 2008, 2008-058007 filed on Mar. 7, 2008, and 2008-058302 filed on Mar. 7, 2008. The entire contents of these applications are incorporated herein by reference.

TECHNICAL FIELD

The present invention relates to an analysis apparatus and a measurement unit, and more particularly, it relates to an analysis apparatus measuring specimens and generating analytical results and a measurement unit employed for the analysis apparatus.

BACKGROUND ART

An analysis apparatus measuring specimens and generating analytical results is known in general. Such an analysis apparatus is disclosed in each of U.S. Pat. Nos. 6,772,650, 7,283,217 and U.S. Patent Laying-Open No. 2007-110617, for example.

In the aforementioned U.S. Pat. No. 6,772,650, a hemanalysis apparatus in which a display and a detecting portion performing detection of specimen samples are stored in one housing (casing) is disclosed.

In the aforementioned U.S. Pat. No. 7,283,217, a sample analysis apparatus including an apparatus body (measurement unit), a sampler portion (transporter) transporting specimen containers to the apparatus body and a data processing terminal including a display portion displaying analytical results is disclosed.

In the aforementioned U.S. Patent Laying-Open No. 2007-110617, a sample analysis apparatus including a sample analysis body apparatus (measurement unit) and a sample container supplying apparatus (transporter) transporting specimen containers to the sample analysis body apparatus is disclosed.

As to institutions such as a hospital and an inspection center using such analysis apparatuses, the scales thereof are diverse. In a small-scale institution, the number of specimens a day is about several to several tens, and hence an analysis apparatus having high treatability for specimens is not necessary but a small-sized and low-priced analysis apparatus is required. In a large-scale institution, on the other hand, the number of specimens a day reaches several hundreds, and hence an analysis apparatus having high treatability for specimens is required even if the same is large-sized and high-priced. For example, an analysis apparatus such as that disclosed in the aforementioned U.S. Pat. No. 6,772,650 is frequently delivered to a small-scale institution, and an analysis apparatus such as that disclosed in the aforementioned U.S. Patent Laying-Open No. 2007-110617 is delivered to a large-scale institution. An analysis apparatus such as that disclosed in the aforementioned U.S. Pat. No. 7,283,217 is frequently delivered to a middle-scale institution.

In order to meet demands from the aforementioned institutions, however, it is necessary to individually develop and design analysis apparatuses such as those shown in the aforementioned U.S. Pat. Nos. 6,772,650, 7,283,217 and U.S. Patent Laying-Open No. 2007-110617 in response to the institution scales, and there has consequently been such problems that it is difficult to render components common to the respective analysis apparatuses and a long time is required for development and a design.

SUMMARY OF THE INVENTION

The present invention has been proposed in order to solve the aforementioned problems, and an object of the present invention is to provide an analysis apparatus capable of flexibly coping in response to the scale of an institution using the analysis apparatus and a measurement unit employed for the analysis apparatus.

In order to attain the aforementioned object, an analysis apparatus according to a first aspect of the present invention is an analysis apparatus measuring specimens and generating analytical results, including a plurality of measurement units of mutually identical types generating measurement data by measuring the specimens, a transporter transporting the specimens to the respective ones of the plurality of measurement units, a display, common to the plurality of measurement units, displaying the analytical results generated by analyzing the measurement data and a transmitter transmitting the analytical results to a host computer.

Preferably, the aforementioned analysis apparatus according to the first aspect further includes a controller, common to the plurality of measurement units, analyzing the measurement data and generating the analytical results, and the controller includes the display and the transmitter.

Preferably in this case, the controller is formed to control operations of the plurality of measurement units.

Preferably in the aforementioned analysis apparatus according to the first aspect, the plurality of measurement units have substantially identical structures.

Preferably, the aforementioned analysis apparatus according to the first aspect includes two measurement units, and the two measurement units include a plurality of identical components, and the identical components are arranged to be symmetrical to each other with respect to a centerline between the two measurement units.

Preferably in the aforementioned analysis apparatus according to the first aspect, the plurality of measurement units are stored in one housing.

Preferably in the aforementioned analysis apparatus according to the first aspect, the transporter is formed to transport a first specimen container, stored in a rack, storing a first specimen to one measurement unit in the plurality of measurement units and to transport a second specimen container, stored in the rack, storing a second specimen to another measurement unit in the plurality of measurement units.

Preferably in the aforementioned analysis apparatus according to the first aspect, the transporter is formed to transport the specimen containers on a single transport path.

Preferably in the aforementioned analysis apparatus according to the first aspect, the display is formed to display information indicating the measurement units having measured the specimens and the generated analytical results in association with each other.

Preferably in this case, the display is formed to display the information indicating the measurement units having measured the specimens and the generated analytical results on the same screen.

Preferably in the aforementioned analysis apparatus according to the first aspect, the transmitter is formed to transmit the analytical results and information indicating the measurement units having measured the specimens to the host computer.

Preferably in the aforementioned analysis apparatus according to the first aspect, the specimens are blood, and the plurality of measurement units are formed to measure the numbers of blood cells in the blood.

Preferably in this case, the plurality of measurement units are formed to generate measurement data for generating at least the numbers of red blood cells, the quantities of hemoglobin, the numbers of platelets and the numbers of white blood cells as the analytical results.

Preferably in the aforementioned analysis apparatus according to the first aspect, the plurality of measurement units are formed to generate measurement data for generating mutually identical measurement items as the analytical results.

A measurement unit according to a second aspect of the present invention is employed for an analysis apparatus including a plurality of measurement units of mutually identical types generating measurement data by measuring specimens, a transporter transporting the specimens to the respective ones of the plurality of measurement units, a display, common to the plurality of measurement units, displaying analytical results generated by analyzing the measurement data and a transmitter transmitting the analytical results to a host computer.

DETAILED DESCRIPTION OF THE PREFERRED EMBODIMENTS

Embodiments of the present invention are now described with reference to the drawings.
(First Embodiment)

First, the overall structure of a hemanalysis apparatus 1 according to a first embodiment of the present invention is described with reference to FIGS. 1 to 8. In the first embodiment, a case of applying the present invention to the hemanalysis apparatus which is an example of the analysis apparatus is described.

Figure 1:
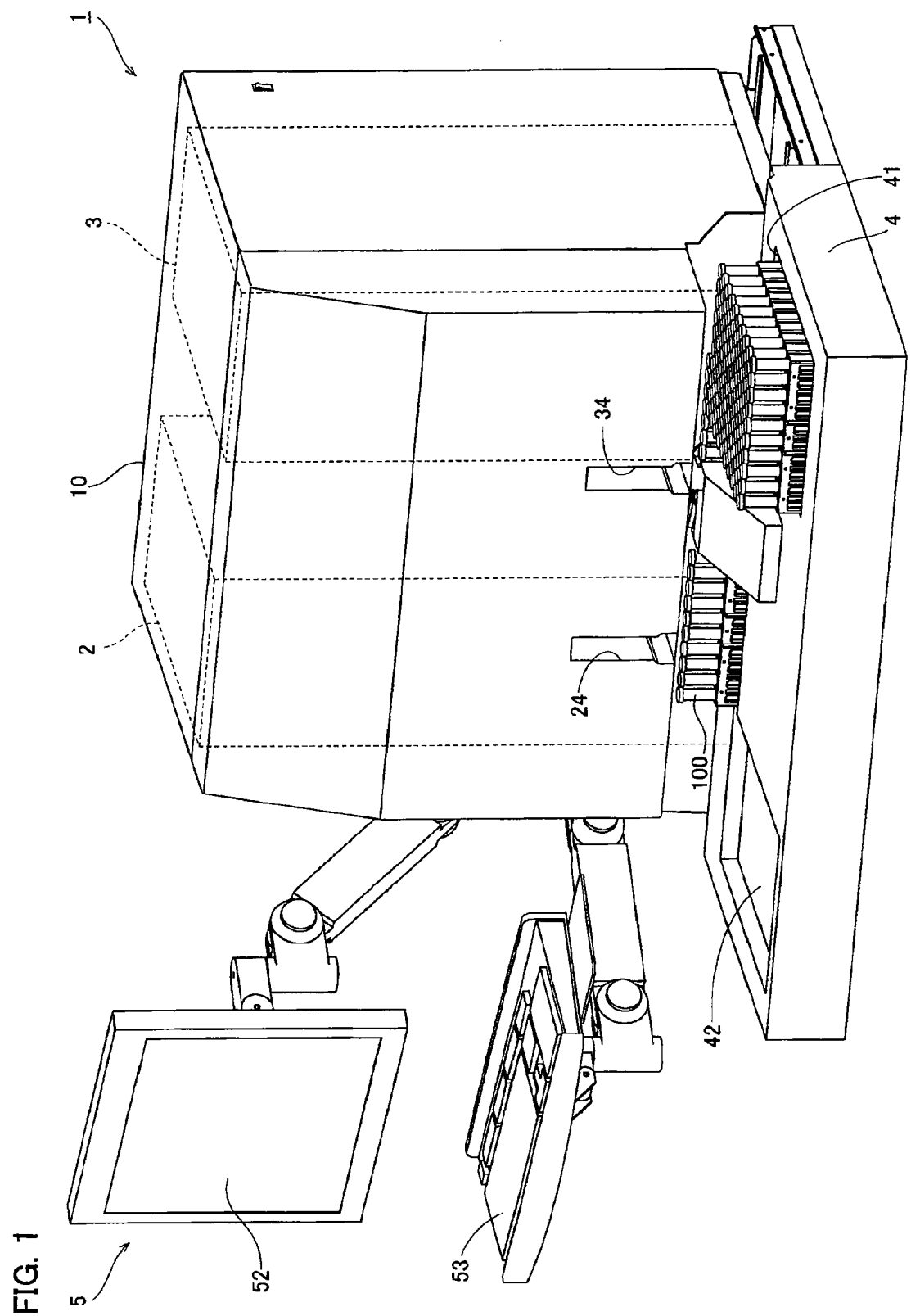
FIG. 1 is a perspective view showing the overall structure of a hemanalysis apparatus according to a first embodiment of the present invention.
Figure 2:
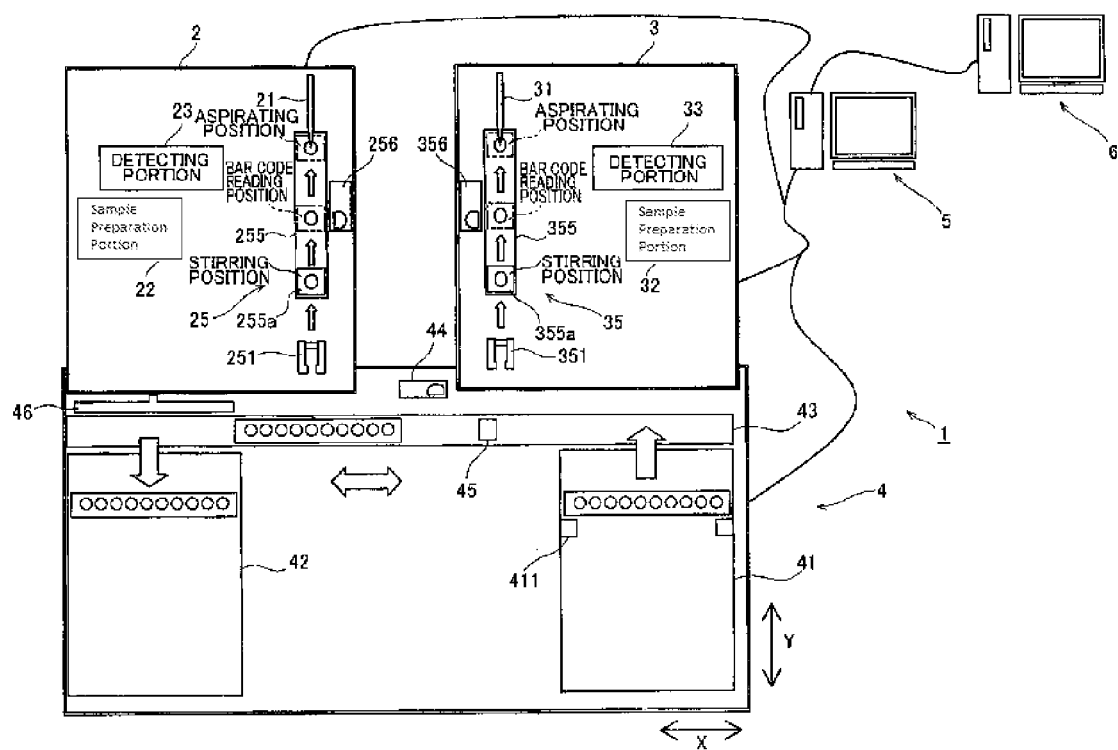
FIG. 2 is a schematic diagram showing measurement units and a specimen transporter of the hemanalysis apparatus according to the first embodiment shown in FIG. 1.

The hemanalysis apparatus 1 according to the first embodiment of the present invention includes two measurement units of a first measurement unit 2 and a second measurement unit 3 of mutually identical types stored in one housing 10 (see FIG. 1), a specimen transporter (sampler) 4 arranged on the side of the front surfaces of the first measurement unit 2 and the second measurement unit 3 and a controller 5 consisting of a PC (personal computer) electrically connected to the first measurement unit 2, the second measurement unit 3 and the specimen transporter 4, as shown in FIGS. 1 and 2. The hemanalysis apparatus 1 is connected to a host computer 6 (see FIG. 2) by the controller 5. The first measurement unit 2 and the second measurement unit 3 are measurement units of the same type, and measure specimens as to the same measurement items by employing the same measurement principle. The same type includes not only a case where the two measurement units measure the specimens as to completely identical measurement items, but also a case where a plurality of measurement items according to the first measurement unit 2 and a plurality of measurement items according to the second measurement unit 3 are partially common. Further, the hemanalysis apparatus 1 is not a transport system connecting a plurality of analysis apparatuses with each other by a conventional transporter, but a stand-alone analysis apparatus. This hemanalysis apparatus 1 may be built into a transport system.

Figure 3:
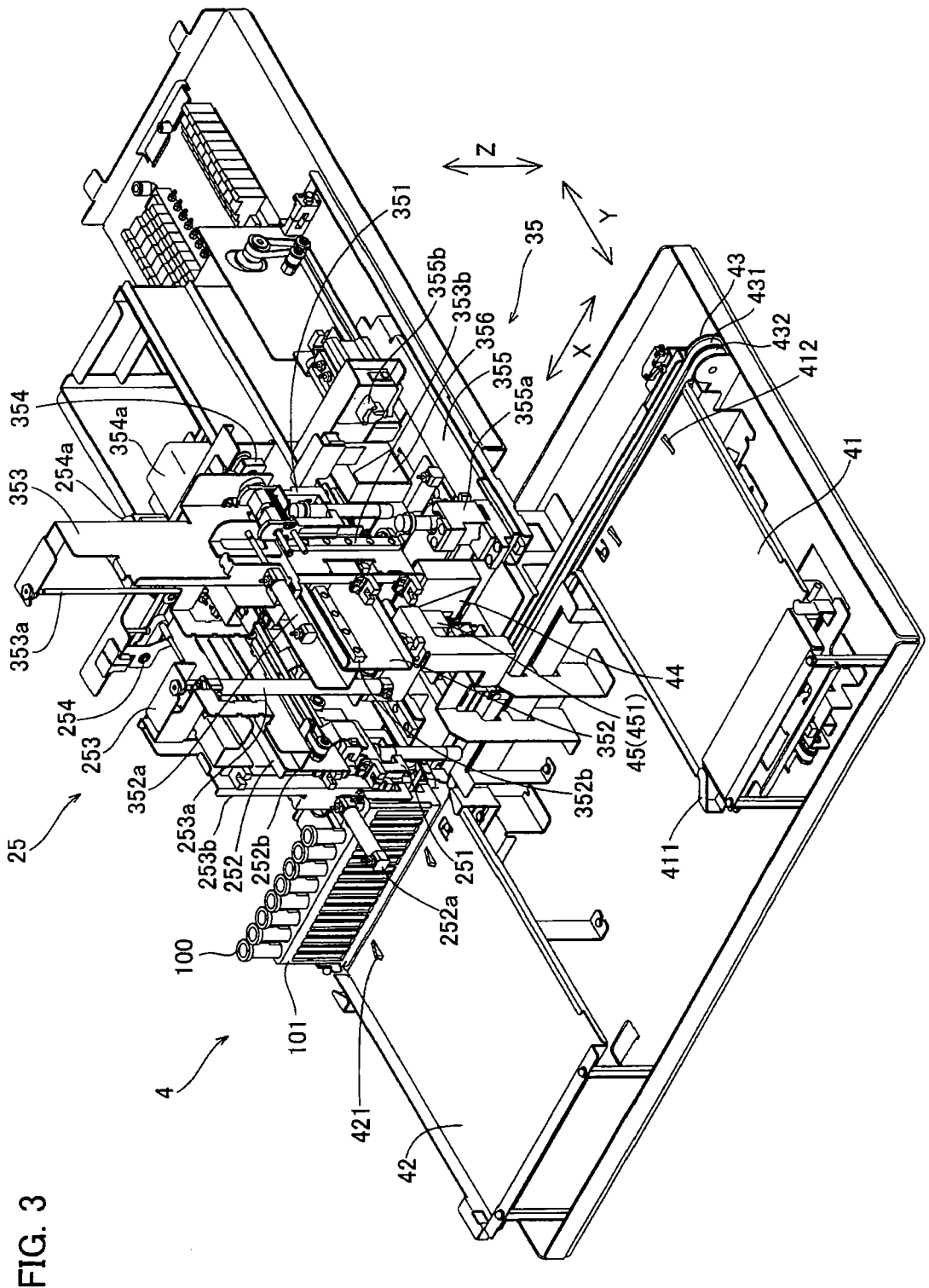
FIG. 3 is a perspective view showing the measurement units and the specimen transporter of the hemanalysis apparatus according to the first embodiment shown in FIG. 1.

The first measurement unit 2 and the second measurement unit 3 have functions of generating measurement data employed for analysis in the controller 5 respectively. As shown in FIGS. 1 to 3, the first measurement unit 2 and the second measurement unit 3 are arranged in the form of mirrors symmetrical with respect to a centerline between the first measurement unit 2 and the second measurement unit 3. As shown in FIG. 2, the first measurement unit 2 and the second measurement unit 3 include specimen aspirating portions 21 and 31 aspirating blood forming specimens from sample containers (test tubes) 100, sample preparation portions 22 and 32 preparing detection samples from the blood aspirated by the specimen aspirating portions 21 and 31, and a detecting portion 23 and a detecting portion 33 detecting blood cells in the blood from the detection samples prepared by the sample preparation portions 22 and 23 respectively. The first measurement unit 2 and the second measurement unit 3 further include sample container transport portions 25 and 35 incorporating the sample containers 100 stored in a rack 101 (see FIG. 4) transported by the specimen transporter 4 thereinto from incorporation ports 24 and 34 (see FIG. 1) provided on the housing 10 and transporting the sample containers 100 to aspirating positions (see FIG. 2) by the specimen aspirating portions 21 and 31 respectively.

Needles (not shown) are provided on the forward end portions of the specimen aspirating portions 21 and 31 respectively. As shown in FIG. 3, the specimen aspirating portions 21 and 31 are formed to be movable in the vertical direction (arrow Z direction) respectively. Further, the specimen aspirating portions 21 and 31 are formed to be moved downward thereby passing through closed lids of the sample containers 100 transported to the aspirating positions and aspirating the inner blood.

The detecting portions 23 and 33 are formed to perform RBC detection (detection of red blood cells) and PLT detection (detection of platelets) by a sheath flow DC detection method and to perform HGB detection (detection of hemoglobin in the blood) by an SLS-hemoglobin method. Further, the detecting portions 23 and 33 are formed to also perform WBC detection (detection of white blood cells) by a flow cytometry method using a semiconductor laser.

Detection results obtained in the detecting portions 23 and 33 are transmitted to the controller 5 as measurement data (measurement results) of the specimens. These measurement data are data forming bases of final analytical results (numbers of red blood cells, numbers of platelets, quantities of hemoglobin, numbers of white blood cells etc.) provided to the user. In other words, the measurement data for generating the numbers of red blood cells, the numbers of platelets, the quantities of hemoglobin, the numbers of white blood cells etc. as analytical results are generated and transmitted to the controller 5 in the first measurement unit 2 and the second measurement unit 3.

The sample container transport portions 25 and 35 respectively have hand portions 251 and 351 capable of grasping the sample containers 100, horizontal moving portions 252 and 352 horizontally linearly moving the hand portions 251 and 351 in an arrow Y direction respectively, vertical moving portions 253 and 353 linearly moving the hand portions 251 and 351 in the vertical direction (arrow Z direction) respectively and stirring portions 254 and 354 pendularly moving the hand portions 251 and 351 in the vertical direction (arrow Z direction) respectively, as shown in FIG. 3. The sample container transport portions 25 and 35 further have sample container moving portions 255 and 355 holding the sample containers 100 acquired from the rack 101 by the hand portions 251 and 351 on specimen set portions 255a and 355a and horizontally linearly moving the same to the aspirating positions of the specimen aspirating portions 21 and 31 in the arrow Y direction and bar code reading portions 256 and 356 respectively.

The hand portions 251 and 351 are formed to move to positions above the sample containers 100 stored in the rack 101 transported by the specimen transporter 4 by moving in the horizontal direction (arrow Y direction) and to thereafter grasp the sample containers 100 present thereunder by moving in the vertical direction (arrow Z direction) respectively. Then, the hand portions 251 and 351 move the grasped sample containers 100 upward, extract the same from the rack 101, and move the same to stirring positions (see FIG. 2) in the horizontal direction (arrow Y direction). The hand portions 251 and 351 are formed to be pendularly moved (by ten round trips, for example) by the stirring portions 254 and 354 on the stirring positions respectively, so that the blood in the grasped sample containers 100 is stirred. The hand portions 251 and 351 are formed to move downward after termination of the stirring thereby setting the sample containers 100 on the specimen set portions 255a and 355a of the sample container moving portions 255 and 355 and opening the grasping.

The horizontal moving portions 252 and 352 are formed to move the hand portions 251 and 351 in the horizontal direction (arrow Y direction) along rails 252b and 352b with power by air cylinders 252a and 352a respectively.

The vertical moving portions 253 and 353 are formed to move the hand portions 251 and 351 in the vertical direction (arrow Z direction) along rails 253b and 353b with power by air cylinders 253a and 353a respectively.

The stirring portions 254 and 354 are formed to pendularly move the hand portions 251 and 351 in the vertical direction (arrow Z direction) with power by stepping motors 254a and 354a respectively.

The sample container moving portions 255 and 355 are formed to transport the specimen set portions 255a and 355a in the arrow Y direction to the aspirating positions with power by unshown stepping motors and to bring the sample containers 100 held on the specimen set portions 255a and 355a into contact with a regulating portion 355b (that on the side of the first measurement unit 2 is not shown) respectively. Thus, the same are formed to clamp (fix) the sample containers 100 on the respective aspirating positions. The sample container moving portions 255 and 355 so move the sample containers 100 to the aspirating positions in plan view that the specimen aspirating portions 21 and 31 can aspirate the samples from the sample containers 100 by simply moving in the vertical direction (arrow Z direction) without moving in the horizontal direction (arrow X and Y directions) respectively.

Figure 4:
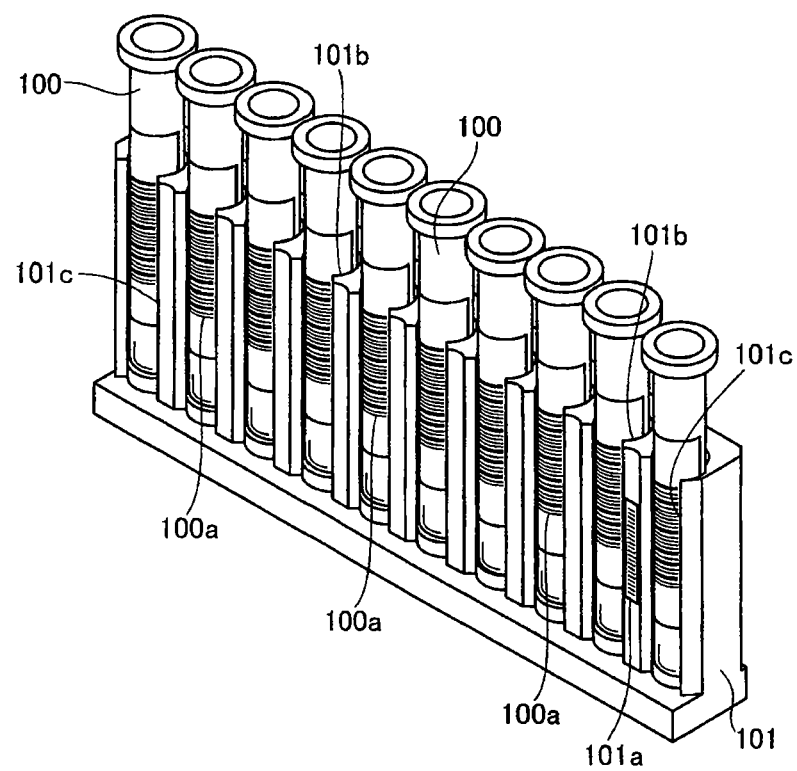
FIG. 4 is a perspective view showing a rack and sample containers of the hemanalysis apparatus according to the first embodiment shown in FIG. 1.

The bar code reading portions 256 and 356 are formed to read bar codes 100a, such as those shown in FIG. 4, pasted to the respective sample containers 100. Further, the bar code reading portions 256 and 356 are formed to read the bar codes 100a of the sample containers 100 while rotating the object sample containers 100 in the horizontal direction by unshown rotators in the state holding the same on the specimen set portions 255a and 355a. Thus, it is possible to direct the bar codes 100a toward the bar code reading portions 256 and 356 by rotating the sample containers 100, also in a case where the bar codes 100a of the sample containers 100 are pasted to opposite sides with respect to the bar code reading portions 256 and 356. The bar codes 100a of the respective sample containers 100 are intrinsically allotted to the respective specimens, and used for management of analytical results of the respective specimens or the like.

Figure 5:
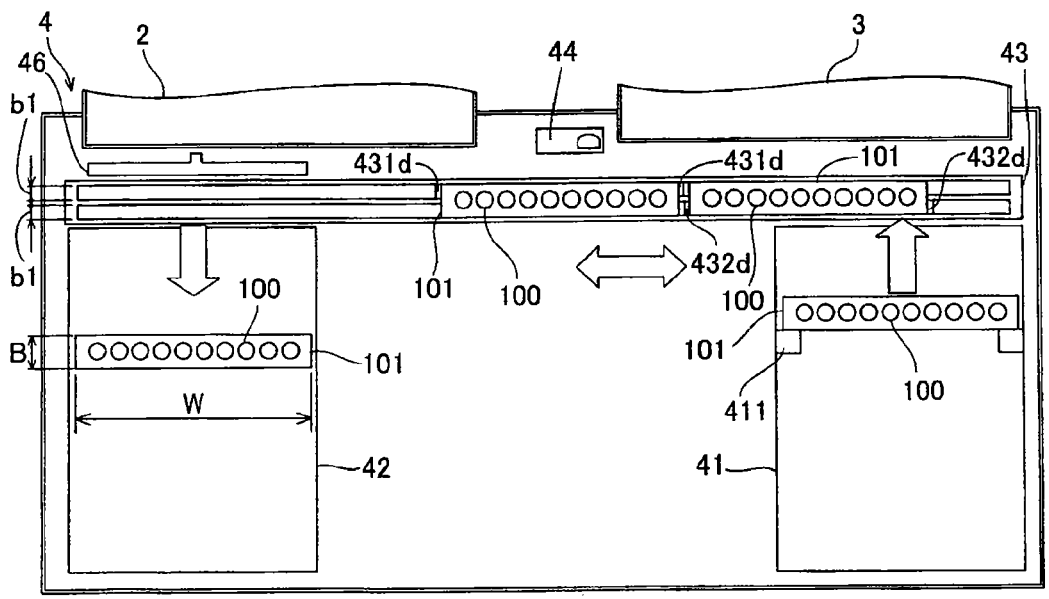
FIG. 5 is a plan view for illustrating the specimen transporter of the hemanalysis apparatus according to the first embodiment shown in FIG. 1.
Figure 6:
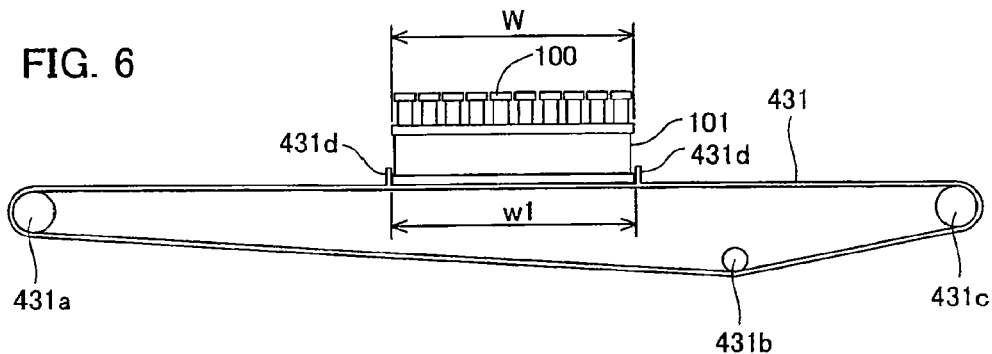
FIG. 6 is a side elevational view for illustrating the specimen transporter of the hemanalysis apparatus according to the first embodiment shown in FIG. 1.
Figure 7:
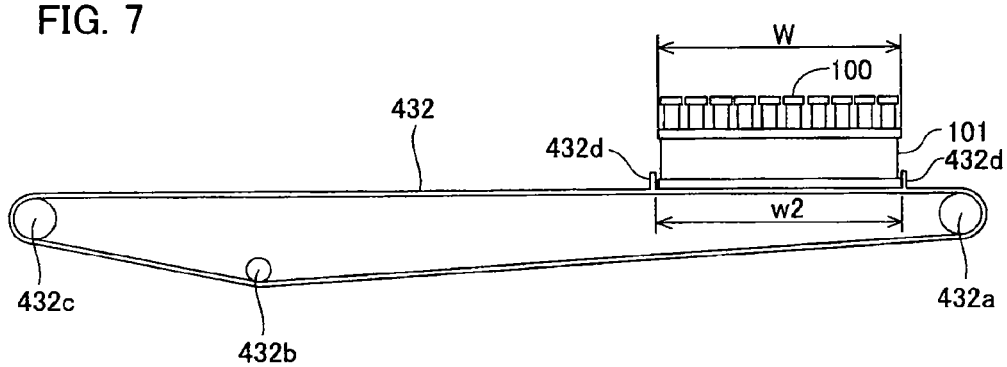
FIG. 7 is a side elevational view for illustrating the specimen transporter of the hemanalysis apparatus according to the first embodiment shown in FIG. 1.

According to the first embodiment, the specimen transporter 4 has a function of transporting the sample containers 100 stored in the rack 101 to prescribed positions of the respective measurement units on a single transport path, in order to transport the specimens to the respective ones of the first measurement unit 2 and the second measurement unit 3. Further, the specimen transporter 4 includes a pre-analysis rack holding portion 41 capable of holding a plurality of racks 101 in which sample containers 100 storing specimens before being analyzed are stored, a post-analysis rack holding portion 42 capable of holding a plurality of racks 101 in which sample containers 100 storing specimens after being analyzed are stored, a rack transport portion 43 horizontally linearly moving the racks 101 in the arrow X direction, a bar code reading portion 44, a presence or absence sensor 45 sensing the presence or absence of the sample containers 100 and a rack delivery portion 46 moving the racks 101 into the post-analysis rack holding portion 42, as shown in FIGS. 3 and 5.

The pre-analysis rack holding portion 41 has a rack feeding portion 411, and is so formed that the rack feeding portion 411 moves in the arrow Y direction thereby pushing out the racks 101 held on the pre-analysis rack holding portion 41 one by one onto the rack transport portion 34. The rack feeding portion 411 is formed to be driven by an unshown stepping motor provided under the pre-analysis rack holding portion 41. The pre-analysis rack holding portion 41 has a regulating portion 412 (see FIG. 3) in the vicinity of the rack transport portion 43, and is formed to regulate movement of each rack 101 so that the rack 101 once pushed out onto the rack transport portion 43 is not returned into the pre-analysis rack holding portion 41.

The post-analysis rack holding portion 42 has a regulating portion 421 (see FIG. 3) in the vicinity of the rack transport portion 43, and is formed to regulate movement of each rack 101 so that the rack 101 once moved into the post-analysis rack holding portion 42 is not returned to the side of the rack transport portion 43.

The rack transport portion 43 has two belts of a first belt 431 and a second belt 432 capable of independently moving respectively. The widths b1 (see FIG. 5) of the first belt 431 and the second belt 432 in the arrow Y direction are not more than the width B of the rack 101 in the arrow Y direction respectively. Thus, both of the first belt 431 and the second belt 432 are parallelly arranged not to jut out from the width B of the rack 101 when the rack transport portion 43 transports the rack 101. Further, the first belt 431 and the second belt 432 are annularly formed, and arranged to surround rollers 431a to 431c and rollers 432a to 432c respectively. On the outer peripheral portions of the first belt 431 and the second belt 432, two protruding segments 431d and two protruding segments 432d are formed respectively to have inner widths w1 (see FIGS. 6) and w2 (see FIG. 7) slightly (by about 1 mm, for example) larger than the width W of the rack 101 in the arrow X direction. The first belt 431 is formed to move the rack 101 in the arrow X direction by being moved on the outer peripheries of the rollers 431 a to 431c by an unshown stepping motor in a state holding the rack 101 inside the protruding segments 431d. More specifically, the protruding segment 431d arranged on the rear side comes into contact with the rack 101 with respect to the direction of movement of the first belt 431, so that the rack 101 is moved in the direction of movement of the first belt 431 in a pushed manner. While the bottom portion of the rack 101 is in contact with the outer peripheral surface of the other second belt 432 when the rack 101 is moved, frictional force between the bottom portion of the rack 101 and the outer peripheral surface of the second belt 432 is extremely small as compared with pressing force by the protruding segment 431d in the direction of movement of the rack 101. Therefore, the first belt 431 can independently move the rack 101, regardless of the presence or absence of movement of the second belt 432. The second belt 432 is formed similarly to the first belt 431.

The bar code reading portion 44 is formed to read the bar codes 100a of the sample containers 100 shown in FIG. 4 and to read a bar code 101a pasted to the rack 101. Further, the bar code reading portion 44 is formed to read the bar codes 100a of the sample containers 100 while horizontally rotating the object sample containers 100 by an unshown rotator in the state storing the same in the rack 101. Thus, it is possible to direct the bar codes 100a toward the bar code reading portion 44 by rotating the sample containers 100, also in a case where the bar codes 100a of the sample containers 100 are pasted to opposite sides with respect to the bar code reading portion 44. The bar code 101a of the rack 101 is intrinsically allotted to each rack, and used for management of the analytical results of the specimens or the like.

The presence or absence sensor 45 is a contact type sensor, and has a curtain-shaped contact segment 451 (see FIG. 3), a light-emitting element (not shown) emitting light and a photoreceiving element (not shown). The presence or absence sensor 45 is so formed that the contact segment 451 is brought into contact with a sensed object of a target of sensing to be bent and the light emitted from the light-emitting element is reflected by the contact segment 451 and introduced into the photoreceiving element as a result. Thus, when any sample container 100 of the target of sensing stored in the rack 101 passes through a portion under the presence or absence sensor 45, the contact segment 451 is so bent by the sample container 100 that it is possible to sense that the sample container 100 is present.

The rack delivery portion 46 is arranged to be opposed to the post-analysis rack holding portion 42 through the rack transport portion 43, and formed to horizontally linearly move in the arrow Y direction. Thus, when the rack 101 is transported to the space (hereinafter referred to as a rack delivery position) between the post-analysis rack holding portion 42 and the rack delivery portion 46, it is possible to press the rack 101 and move the same into the post-analysis rack holding portion 42 by moving the rack delivery portion 46 toward the post-analysis rack holding portion 42.

Figure 8:
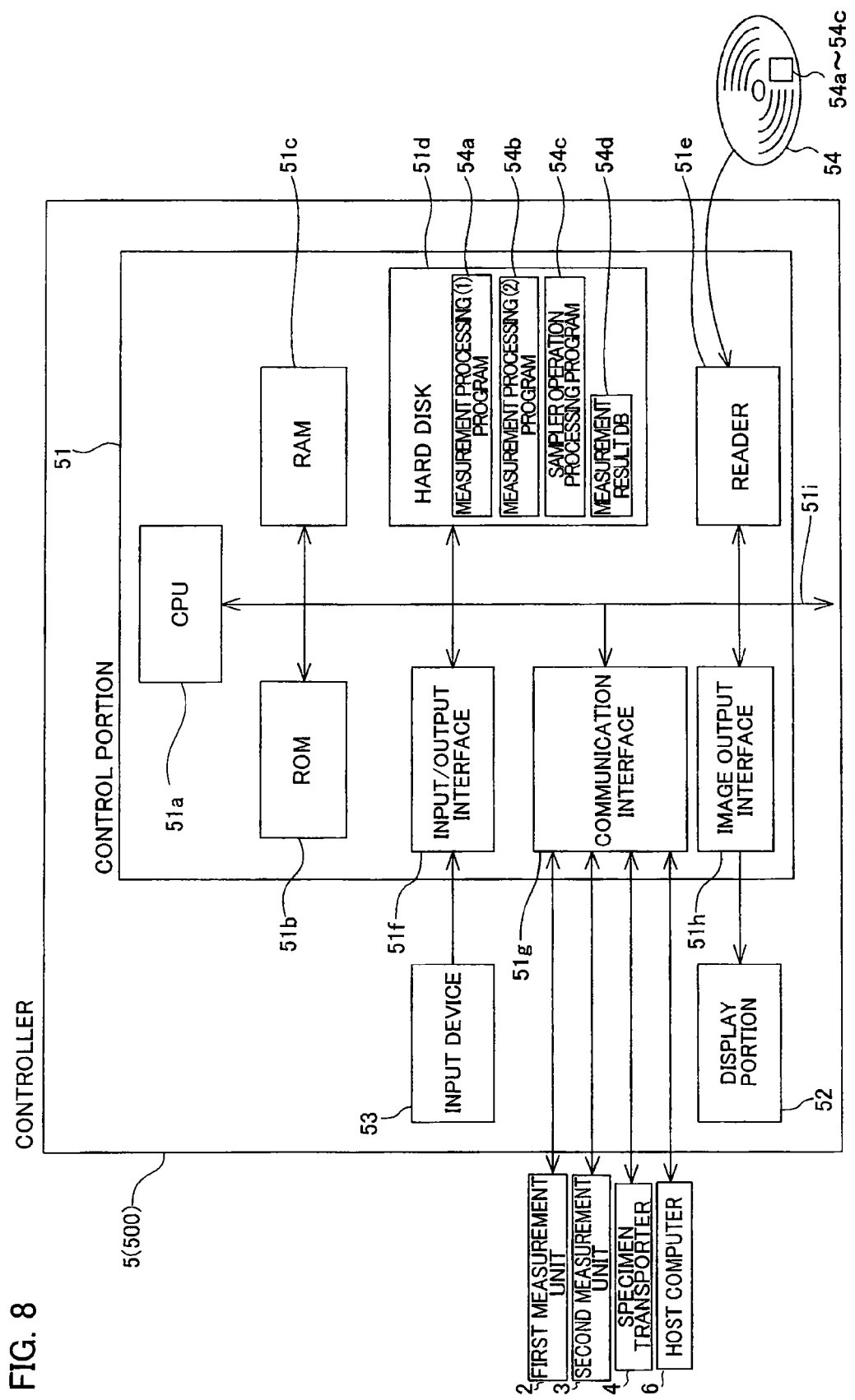
FIG. 8 is a block diagram for illustrating a controller of the hemanalysis apparatus according to the first embodiment shown in FIG. 1.

The controller 5 consists of a personal computer (PC) or the like, and includes a control portion 51 consisting of a CPU, a ROM, a RAM etc., a display portion 52 and an input device 53, as shown in FIGS. 1 and 8. The control portion 5 is provided in order to control operations of both of the first measurement unit 2 and the second measurement unit 3.

The structure of the controller 5 is now described. The controller 5 is constituted of a computer 500 mainly constituted of the control portion 51, the display portion 52 and the input device 53, as shown in FIG. 8. The control portion 51 is mainly constituted of a CPU 51a, a ROM 51b, a RAM 51c, a hard disk 51d, a reader 51e, an input/output interface 51f, a communication interface 51g and an image output interface 51h. The CPU 51a, the ROM 51b, the RAM 51c, the hard disk

51d, the reader 51e, the input/output interface 51f, the communication interface 51g and the image output interface 51h are connected with each other by a bus 51i.

The CPU 51a is capable of running computer programs stored in the ROM 51b and computer programs loaded in the RAM 51c. The CPU 51a so runs application programs 54a to 54c described later that the computer 500 functions as the controller 5.

The ROM 51b is constituted of a mask ROM, a PROM, an EPROM, an EEPROM or the like, in which the computer programs run by the CPU 51a and data employed therefor are recorded.

The RAM 51c is constituted of an SRAM or a DRAM. The RAM 51c is employed for reading the computer programs recorded in the ROM 51b and the hard disk 51d. Further, the same is utilized as a working area of the CPU 51a when running these computer programs.

Various computer programs such as an operating system and application programs to be run by the CPU 51a and data employed for running the computer programs are installed in the hard disk 51d. A measurement processing program 54a for the first measurement unit 2, a measurement processing program 54b for the second measurement unit 3 and a measurement processing program 54c for the specimen transporter 4 are also installed in this hard disk 51d. These application programs 54a to 54c are so run by the CPU 51a that operations of the respective portions of the first measurement unit 2, the second measurement unit 3 and the specimen transporter 4 are controlled. A measurement result database 54d is also installed.

The reader 51e is constituted of a flexible disk drive, a CD-ROM drive or a DVD-ROM drive, and can read computer programs or data recorded in a portable recording medium 54. The application programs 54a to 54c are stored in the portable recording medium 54, and the computer 500 is capable of reading the application programs 54a to 54c from the portable recording medium 54 and installing the application programs 54a to 54c in the hard disk 51d.

The aforementioned application programs 54a to 54c are not only provided by the portable recording medium 54, but can also be provided from an external apparatus communicatively connected with the computer 500 by an electric communication line (irrespective of wired or wireless) through the aforementioned electric communication line. For example, the aforementioned application programs 54a to 54c may be stored in a hard disk of a server computer on the Internet, so that the computer 500 can download the application programs 54a to 54c and install the same in the hard disk 51d by accessing this server computer.

An operating system such as Windows (registered trademark) manufactured and sold by Microsoft Corporation, U.S.A., for example, providing a graphical user interface environment is installed in the hard disk 51d. In the following description, it is assumed that the application programs 54a to 54c operate on the aforementioned operating system.

The input/output interface 51 is constituted of a serial interface such as USB, IEEE1394 or RS-232C, a parallel interface such as SCSI, IDE or IEEE1284, or an analog interface consisting of a D/A converter, an A/D converter etc., for example. The input device 53 is connected to the input/output interface 51f, and the user can input data in the computer 500 by using the input device 53.

The communication interface 51g is an Ethernet (registered trademark) interface, for example. With the communication interface 51g, the computer 500 can transmit/receive data between the same and the first measurement unit 2, the second measurement unit 3, the specimen transporter 4 and the host computer 6 by using a prescribed communication protocol.

The image output interface 51h is connected to the display portion 52 constituted of an LCD or a CRT, and formed to output image signals responsive to image data supplied from the CPU 51a to the display portion 52. The display portion 52 displays images (screen) of the analytical results etc. according to the input image signals.

The control portion 51 is formed to analyze components of analytical objects with measurement results transmitted from the first measurement unit 2 and the second measurement unit 3 and to acquire analytical results (numbers of red blood cells, numbers of platelets, quantities of hemoglobin, numbers of white blood cells etc.), due to the aforementioned structure.

The rack 101 is provided with ten container storing portions 101b, to be capable of storing ten sample containers 100 in alignment. Openings 101c are provided on the respective container storing portions 101b, so that the bar codes 100a of the stored sample containers 100 are visually recognizable respectively.

Figures 9, 10:
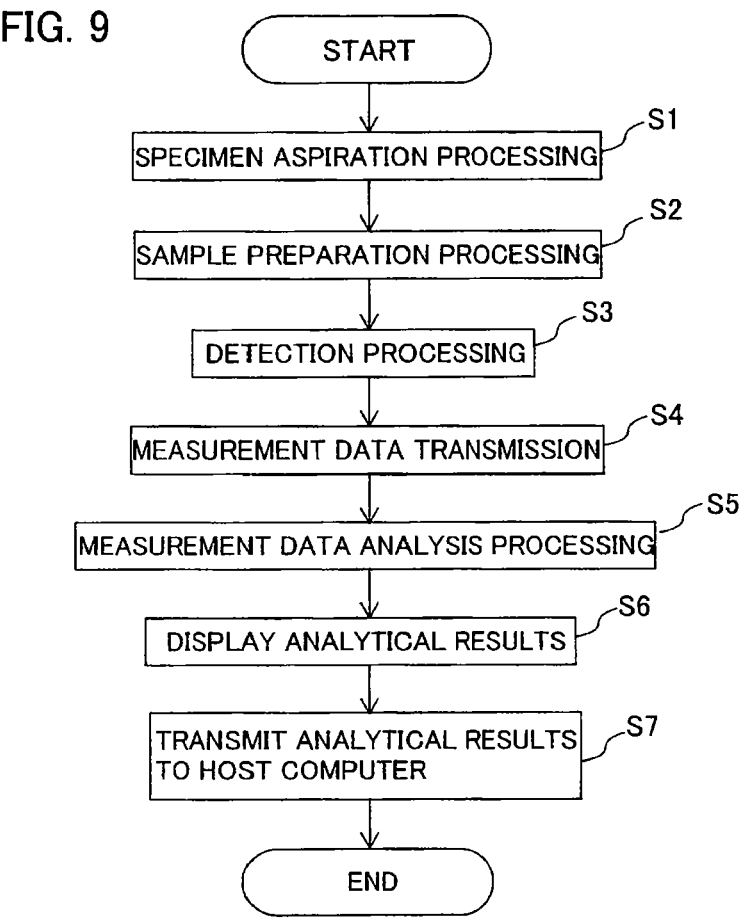
FIG. 9 is a flow chart for illustrating a measurement processing operation according to a measurement processing program of the hemanalysis apparatus according to the first embodiment shown in FIG. 1.
FIG. 10 is a diagram showing a screen of analytical results of the hemanalysis apparatus according to the first embodiment shown in FIG. 1.
Figure 11:
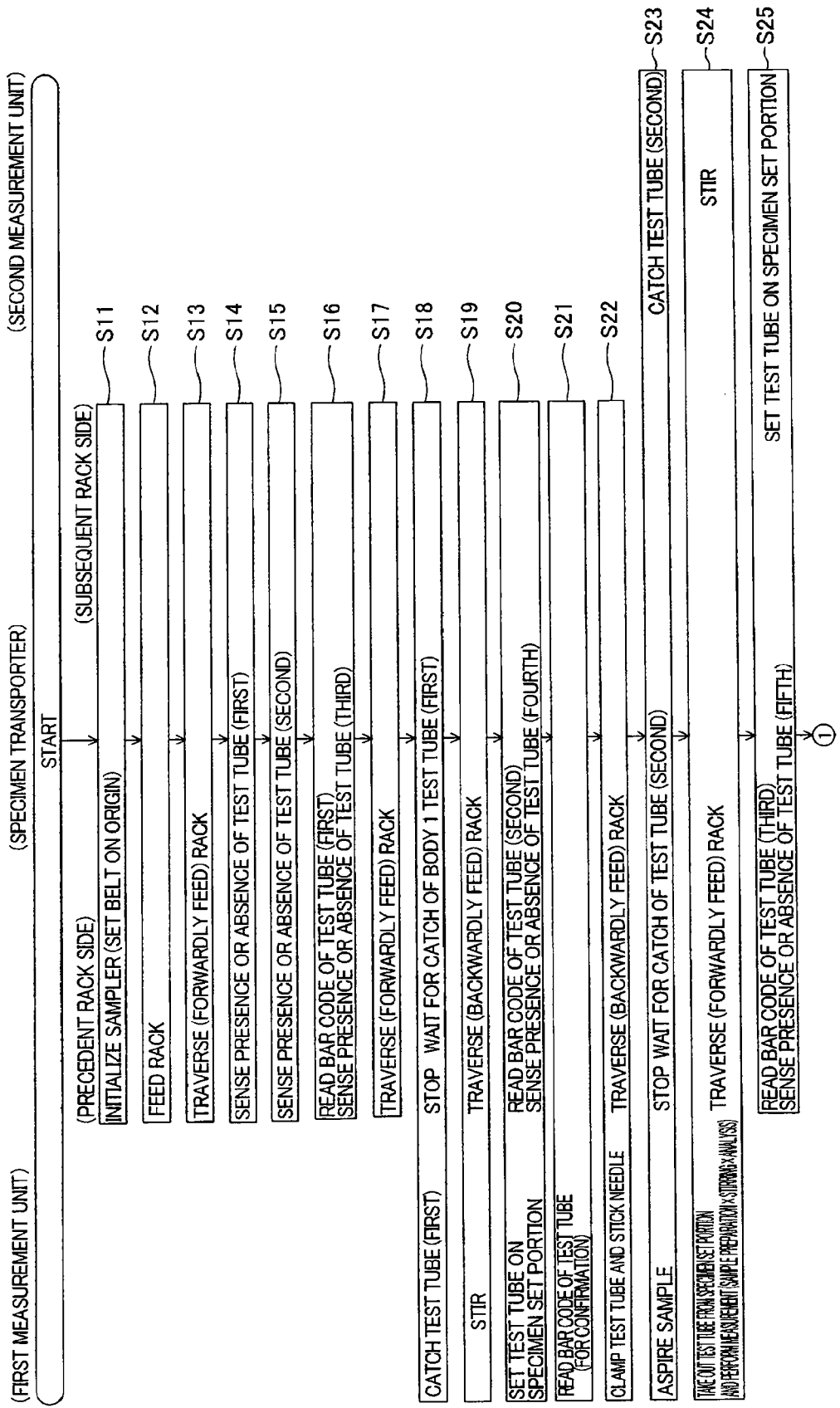
FIG. 11 is a flow chart for illustrating the contents of a measurement processing (1) program 54a, a measurement processing (2) program 54b and a sampler operation processing program 54c.
Figure 12:
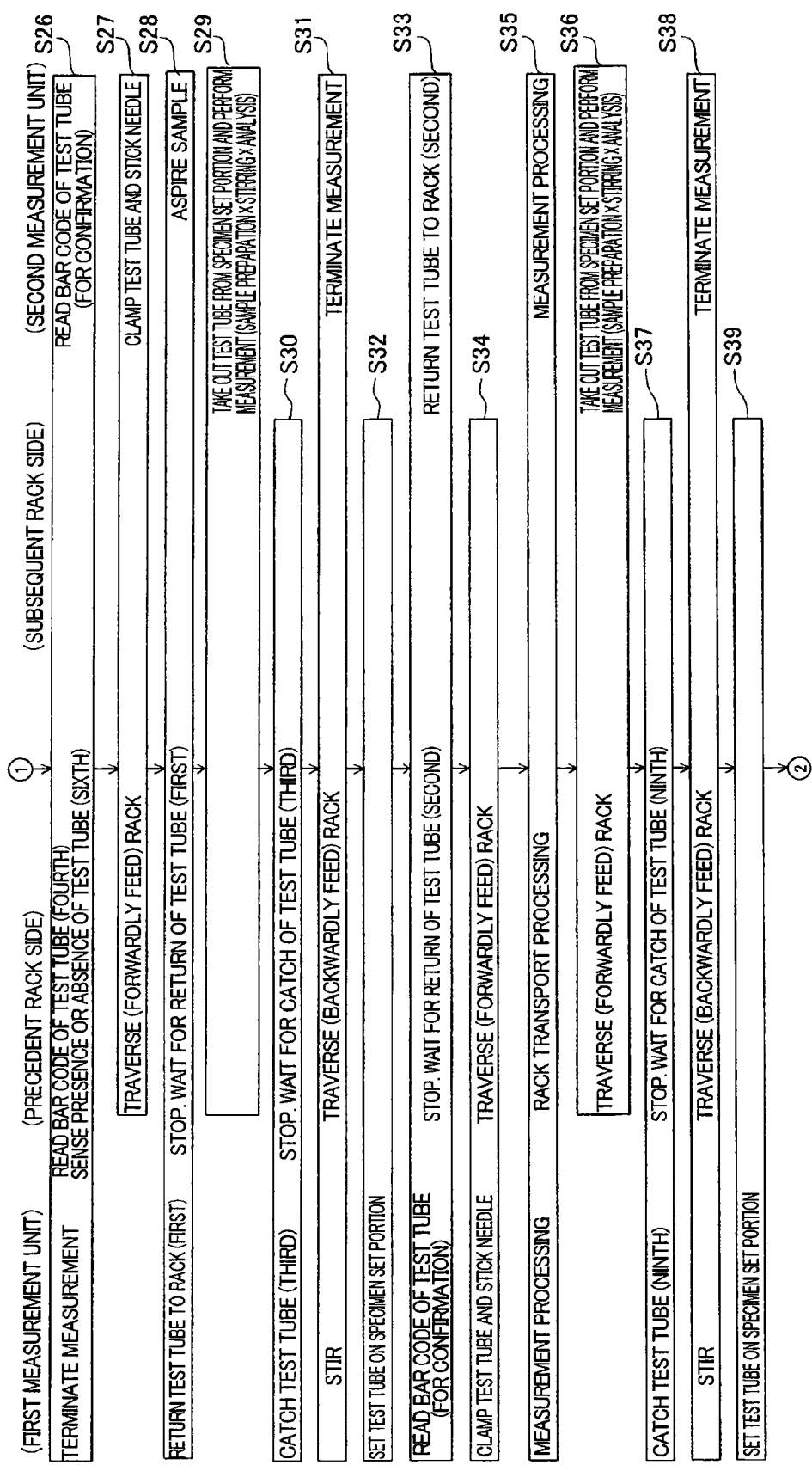
FIG. 12 is a flow chart for illustrating the contents of the measurement processing (1) program 54a, the measurement processing (2) program 54b and the sampler operation processing program 54c.
Figure 13:
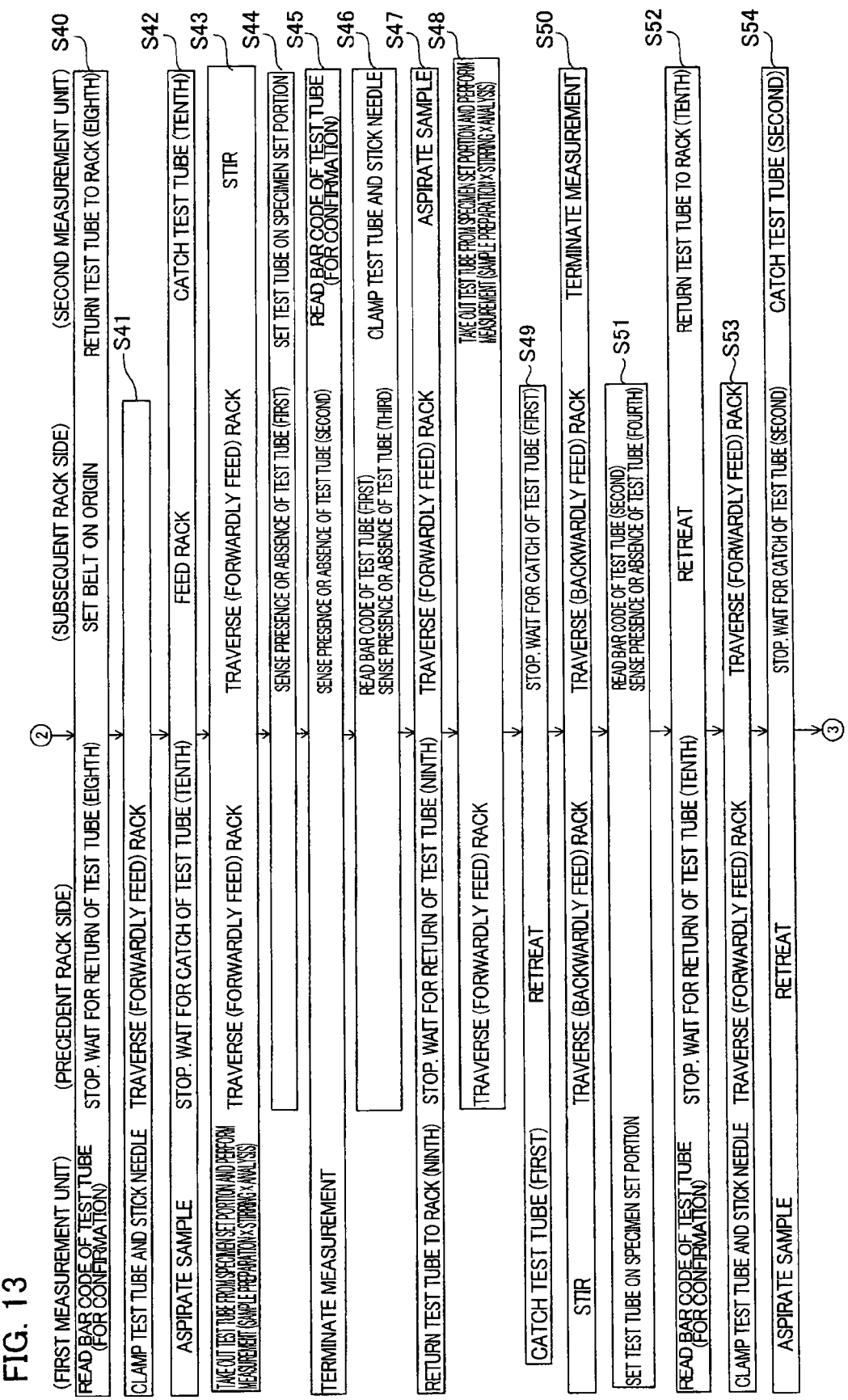
FIG. 13 is a flow chart for illustrating the contents of the measurement processing (1) program 54a, the measurement processing (2) program 54b and the sampler operation processing program 54c.
Figure 14:
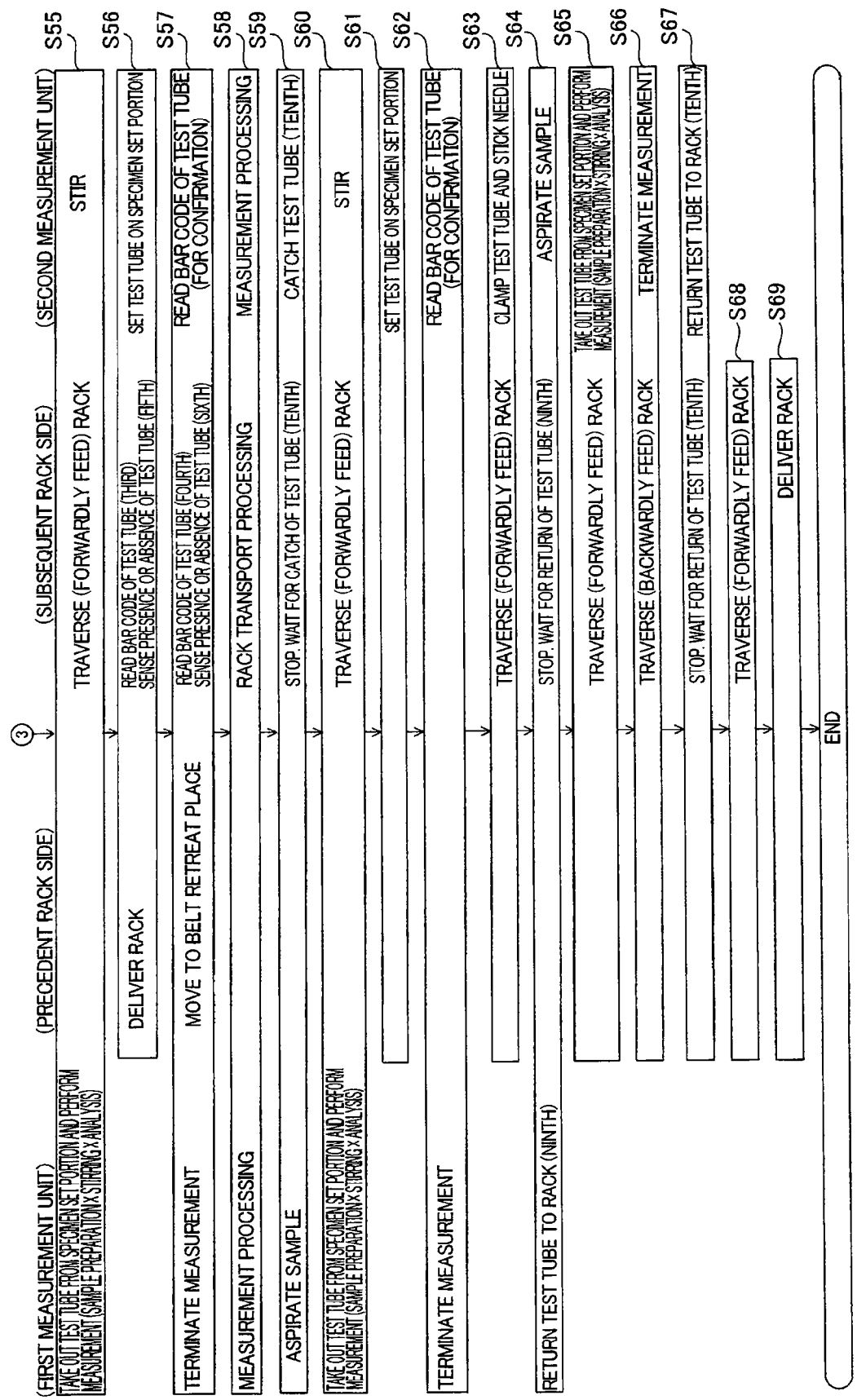
FIG. 14 is a flow chart for illustrating the contents of the measurement processing (1) program 54a, the measurement processing (2) program 54b and the sampler operation processing program 54c.

Measurement processing operations of the hemanalysis apparatus 1 according to the first embodiment with the measurement processing programs 54a and 54b are now described with reference to FIGS. 2, 9 and 10. Components of analytical objects are similarly measured in the first measurement unit 2 and the second measurement unit 3, and hence a case of measuring the components of any analytical object with the first measurement unit 2 is now typically described.

First, aspiration of the specimen is performed by the specimen aspirating portion 21 from any sample container 100 transported to the aspirating position (see FIG. 2) at a step S1. Then, a detection sample is prepared from the aspirated specimen by the sample preparation portion 22 at a step S2, and the components of the analytical object are detected from the detection sample by the detecting portion 23 at a step S3. Then, measurement data are transmitted from the first measurement unit 2 to the controller 5 at a step S4, and the components of the analytical object are analyzed by the control portion 51 on the basis of the transmitted measurement results at a step S5. Thereafter a screen of the analytical results is displayed on the display portion 52 at a step S6 as shown in FIG. 10, and specimen number information, information of the analytical results (the numbers of red blood cells (RBC), the numbers of platelets (PLT), the quantities of hemoglobin (HBC), the numbers of white blood cells (WBC) etc.) and measurement unit number information indicating the measurement unit in which the measurement has been performed are transmitted from the controller 5 to the host computer 6 at a step S7. On the screen of the analytical results shown in FIG. 10, the specimen number, the analytical results (the number of red blood cells (RBC), the number of platelets (PLT), the quantity of hemoglobin (HBC), the number of white blood cells (WBC) etc.) and the measurement unit number are displayed on the same screen to correspond to each other every specimen.

Figure 15:
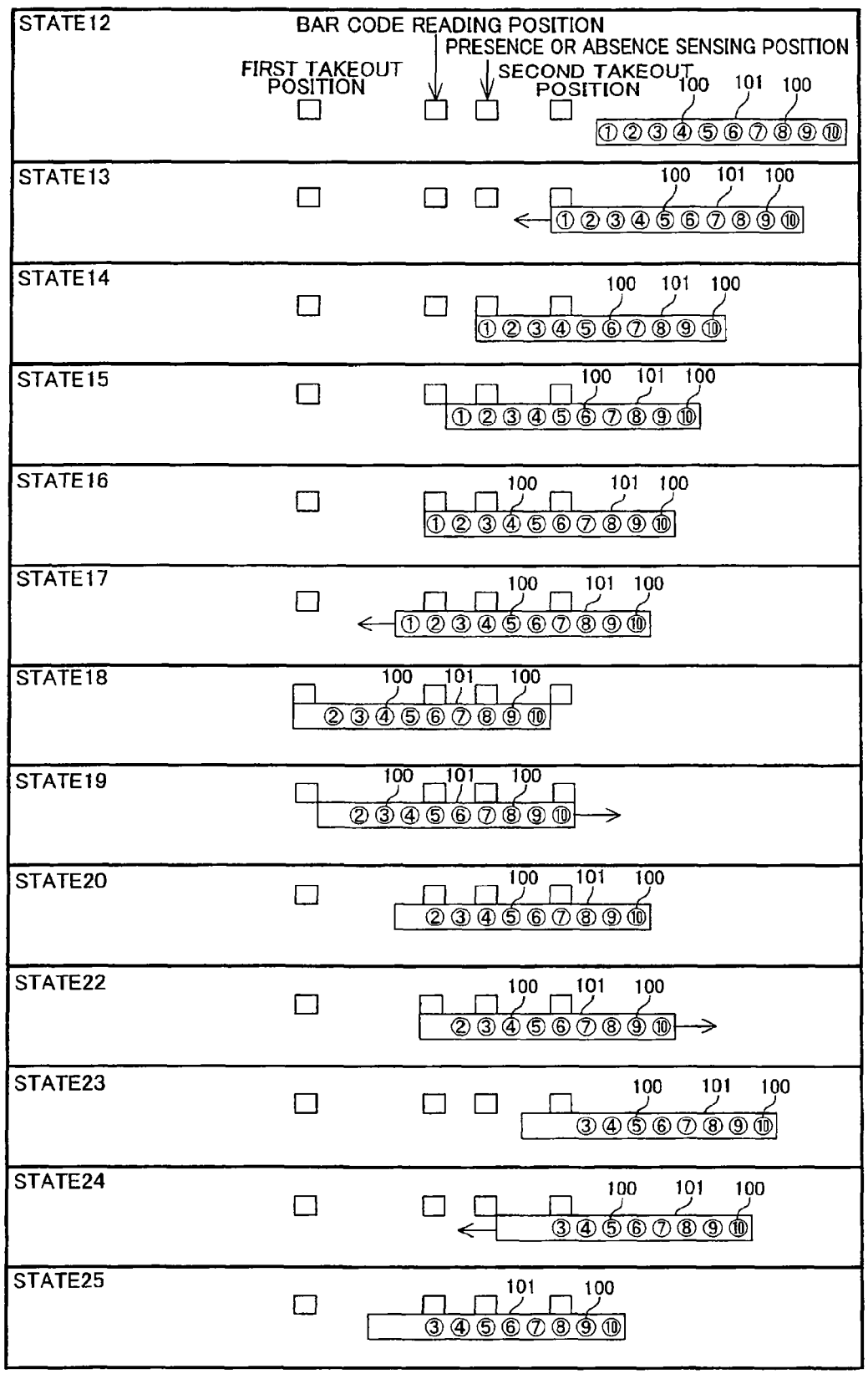
FIG. 15 is a diagram showing positional relations between the rack and the sample containers and respective portions of the hemanalysis apparatus according to the first embodiment shown in FIG. 1.
Figure 16:
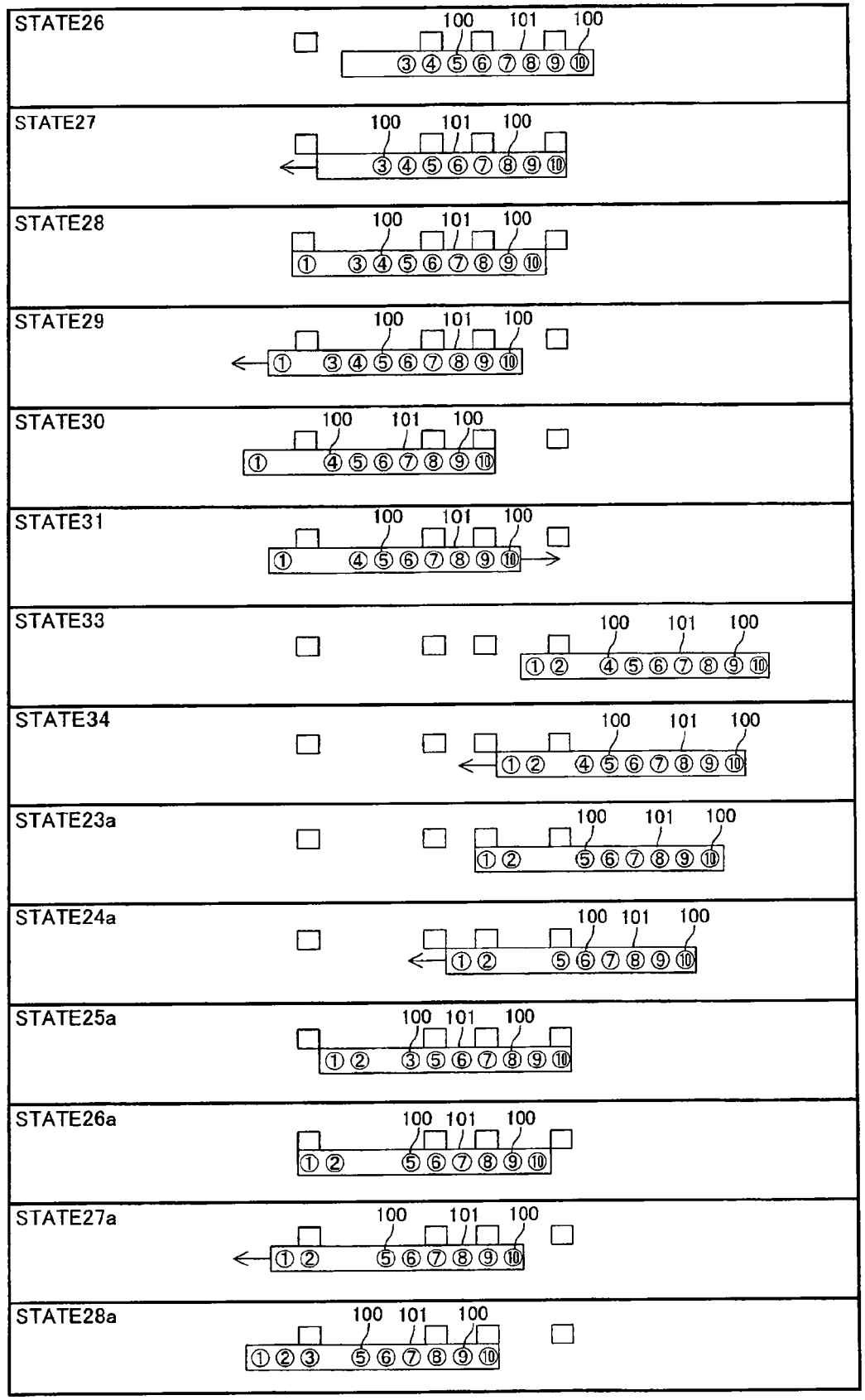
FIG. 16 is a diagram showing positional relations between the rack and the sample containers and the respective portions of the hemanalysis apparatus according to the first embodiment shown in FIG. 1.
Figure 17:
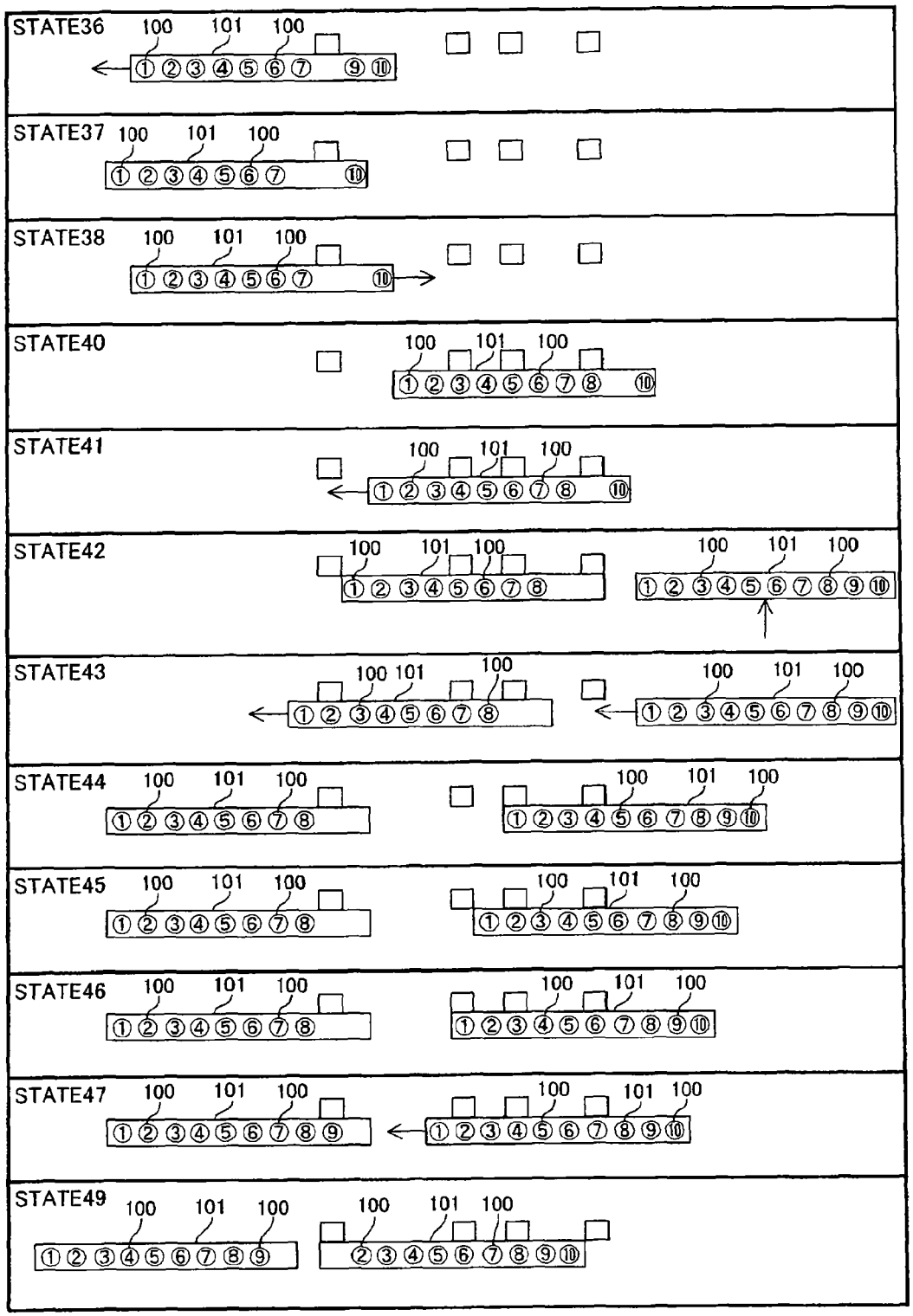
FIG. 17 is a diagram showing positional relations between racks and the sample containers and the respective portions of the hemanalysis apparatus according to the first embodiment shown in FIG. 1.
Figure 18:
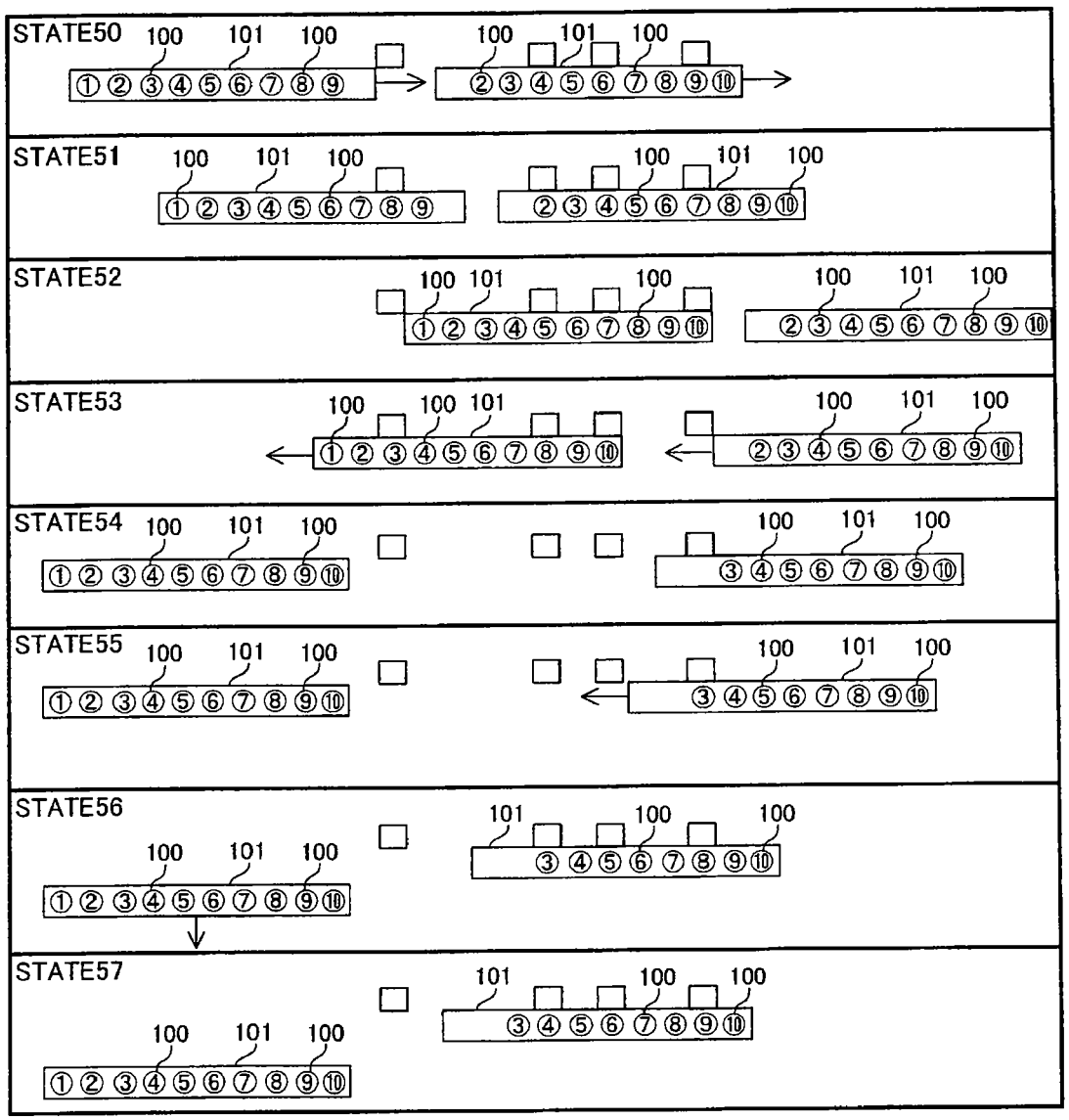
FIG. 18 is a diagram showing positional relations between the racks and the sample containers and the respective portions of the hemanalysis apparatus according to the first embodiment shown in FIG. 1.

A series of operations of the first measurement unit 2, the second measurement unit 3 and the specimen transporter 4 of the hemanalysis apparatus 1 according to the first embodiment are now described with reference to FIGS. 11 to 18. In flow charts of FIGS. 11 to 14, the contents of the measurement processing (1) program 54a are shown in the left columns and the contents of the measurement processing (2) program 54b are shown in the right columns, while the contents of the sampler operation processing program 54c are shown in the central columns. As to the sampler operation processing program 54c, processing contents related to a precedent rack 101 are shown in the left central columns, and processing contents related to a subsequent rack 101 are shown in the right central columns. The precedent rack 101 denotes a rack 101 precedently fed into the rack transport portion 43 from the pre-analysis rack holding portion 41, and the subsequent rack 101 denotes a rack 101 subsequently fed in the state where the precedent rack 101 is present on the rack transport portion 43. Numbers of respective states showing the positional relations between the racks 101 and the sample containers 100 and respective portions shown in FIGS. 15 to 18 are allotted to correspond to step numbers shown in FIGS. 11 to 14 respectively. For example, the positional relation between the rack 101 and the sample containers 100 and the respective portions in a state 13 in FIG. 15 is the positional relation between the rack 101 and the sample containers 100 and the respective portions in a step S13 shown in FIG. 11. As shown in FIGS. 11 to 14, the measurement processing (1) program 54a, the measurement processing (2) program 54b and the sampler operation processing program 54c are run substantially in parallel with each other.

First, when the hemanalysis apparatus 1 is started by the user, initialization of the specimen transporter 4 is performed at a step S11. At this time, the protruding segments 431d of the first belt 431 are moved to prescribed positions, and set as an origin position of the first belt 431. At a step S12, the two protruding segments 431d are moved to a position (hereinafter referred to as a rack feeding position) opposed to the pre-analysis rack holding portion 41, and the precedent rack 101 is fed into the space between the two protruding segments 431d of the first belt 431. The positional relation between the rack 101 and the sample containers 100 and the respective portions at this time is the same as a state 12 in FIG. 15. In the following, description of the positional relations between the racks 101 and the sample containers 100 and the respective portions in the respective states shown in FIGS. 15 to 18 is omitted. In the first embodiment, a case where first to tenth sample containers 100 are stored in each rack 101 successively from the front side toward the rear side with respect to a forward feeding direction is described, as shown in FIGS. 15 to 18.

The precedent rack 101 is moved in the direction (forward feeding direction) of the first measurement unit 2 at the step S13, and the presence or absence of the first sample container 100 stored in the precedent rack 101 is sensed by the presence or absence sensor 45 at a step S14. Then, the presence or absence of the second sample container 100 is sensed at a step S15, and the bar code 100a of the first sample container 100 is read by the bar code reading portion 44 and the presence or absence of the third is sensed at a step S16. Sensing results sensed by the presence or absence sensor 45 and bar code information read by the bar code reading portions 44, 256 and 356 are transmitted to the host computer 6 at any time. At a step S17, the precedent rack 101 is moved to a first takeout position (see FIG. 15) where the first sample container 100 is taken out from the precedent rack 101 by the hand portion 251 of the first measurement unit 2 (in other words, the first sample container 100 is transported to the first measurement unit 2). At this time, the bar code 101a of the rack 101 is read by the bar code reading portion 44. At a step S18, the first sample container 100 is taken out from the precedent rack 101 by the hand portion 251 of the first measurement unit 2. At this time, the precedent rack 101 is at a stop on a position where the first sample container 100 corresponds to the first takeout position. At a step S19, the specimen in the first sample container 100 grasped by the hand portion 251 is stirred in the first measurement unit 2, while the precedent rack 101 from which the first sample container 100 has been taken out is moved in a backward feeding direction opposite to the forward feeding direction.

At a step S20, the first sample container 100 is set on the specimen set portion 255a in the first measurement unit 2, while the bar code 100a of the second in the precedent rack 101 is read and the presence or absence of the fourth sample container 100 is sensed. The bar code 100a of the first sample container 100 is read by the bar code reading portion 256 in the first measurement unit 2 at a step S21, and the first sample container 100 held on the specimen set portion 255a is brought into contact with the regulating portion (not shown) and clamped while the needle (not shown) of the specimen aspirating portion 21 is stuck and passed into the closed lid of the sample container 100 at a step S22. At this time, the precedent rack 101 is moved to a second takeout position (see FIG. 15) where the second sample container 100 is taken out from the precedent rack 101 by the hand portion 351 of the second measurement unit 3 (in other words, the second sample container 100 is transported to the second measurement unit 3). Reading of the bar codes 100a of the sample containers 100 by the bar code reading portions 256 and 356 is performed as that for confirmation of reading by the bar code reading portion 44. Thereafter at a step S23, aspiration of the specimen in the first sample container 100 is performed by the specimen aspirating portion 21 in the first measurement unit 2, while the second sample container 100 is taken out from the precedent rack 101 by the hand portion 351 of the second measurement unit 3.

At a step S24, the first sample container 100 is taken out from the specimen set portion 255a by the hand portion 251 while sample preparation, stirring and analysis are performed as to the specimen aspirated by the specimen aspirating portion 21 in the first measurement unit 2. Further, the specimen in the second sample container 100 grasped by the hand portion 351 is stirred in the second measurement unit 3, while the precedent rack 101 is moved in the forward feeding direction. At a step S25, the second sample container 100 is set on the specimen set portion 355a in the second measurement unit 3, while the bar code 100a of the third in the precedent rack 101 is read and the presence or absence of the fifth sample container 100 is sensed. At a step S26, the measurement as to the specimen in the first sample container 100 is terminated in the first measurement unit 2, and the bar code 100a of the second sample container 100 is read by the bar code reading portion 356 in the second measurement unit 3. Further, the bar code 100a of the fourth in the precedent rack 101 is read, and the presence or absence of the sixth sample container 100 is sensed. In this description, the wording "the measurement as to the specimen is terminated" denotes transmission completion of the measurement data at the step S4 shown in FIG. 9. In other words, analytical processing (analysis) of the measurement data through the step S5 is not yet completed even if the measurement as to the specimen in the first sample container 100 is terminated at the step S26.

At a step S27, the second sample container 100 held on the specimen set portion 355a is brought into contact with the regulating portion 355b and clamped, while the needle (not shown) of the specimen aspirating portion 31 is stuck and passed into the closed lid of the sample container 100. At this time, the precedent rack 101 is moved in the forward feeding direction. At a step S28, the first sample container 100 is returned from the first measurement unit 2 into the original container storing portion 101b of the precedent rack 101, while aspiration of the specimen in the second sample container 100 is performed by the specimen aspirating portion 31 in the second measurement unit 3. At a step S29, the second sample container 100 is taken out from the specimen set portion 355*a* by the hand portion 351 and sample preparation, stirring and analysis are performed as to the specimen aspirated by the specimen aspirating portion 31 in the second measurement unit 3. The precedent rack 101 is moved in the forward feeding direction. At a step S30, the third sample container 100 is taken out from the precedent rack 101 by the hand portion 251 of the first measurement unit 2. At this time, the precedent rack 101 is at a stop on a position where the third sample container 100 corresponds to the first takeout position. At a step S31, the specimen in the third sample container 100 grasped by the hand portion 251 is stirred in the first measurement unit 2, while the precedent rack 101 is moved in the backward feeding direction. In the second measurement unit 3, the measurement as to the specimen in the second sample container 100 is terminated.

Then, the third sample container 100 is set on the specimen set portion 255*a* in the first measurement unit 2 at a step S32, and the bar code 100*a* of the third sample container 100 is read by the bar code reading portion 256 in the first measurement unit 2 at a step S33. Further, the second sample container 100 is returned from the second measurement unit 3 into the original container storing portion 101*b* of the precedent rack 101. At a step S34, the third sample container 100 is clamped, while the needle (not shown) of the specimen aspirating portion 21 is stuck and passed into the closed lid of the sample container 100. The precedent rack 101 is moved in the forward feeding direction. Also as to the following sample containers 100, measurement processing is performed in the first measurement unit 2 and the third measurement unit 3 and transport processing for the precedent rack 101 is performed in the specimen transporter 4, similarly to the above. The drawings are simplified since similar processing is repeated, and it is shown that prescribed processing is performed in each portion at a step S35. The positional relations between the precedent rack 101 and the sample containers 100 and the respective portions corresponding to the steps S23 to S28 in the repetitive processing are shown in states 23*a* to 28*a* in FIG. 16.

At a step S36, the eighth sample container 100 is taken out from the specimen set portion 355*a* by the hand portion 351 and sample preparation, stirring and analysis are performed as to the specimen aspirated by the specimen aspirating portion 31 in the second measurement unit 3. The precedent rack 101 is moved in the forward feeding direction. At a step S37, the ninth sample container 100 is taken out from the precedent rack 101 by the hand portion 251 of the first measurement unit 2. At this time, the precedent rack 101 is at a stop on a position where the ninth sample container 100 corresponds to the first takeout position. At a step S38, the specimen in the ninth sample container 100 is stirred in the first measurement unit 2, while the precedent rack 101 is moved in the backward feeding direction. In the second measurement unit 3, the measurement as to the specimen in the eighth sample container 100 is terminated.

The ninth sample container 100 is set on the specimen set portion 255*a* in the first measurement unit 2 at a step S39, and the bar code 100*a* of the ninth sample container 100 is read by the bar code reading portion 256 in the first measurement unit 2 at a step S40. Further, the eighth sample container 100 is returned from the second measurement unit 3 into the original container storing portion 101*b* of the precedent rack 101. In addition, the protruding segments 432*d* of the second belt 432 are moved to prescribed positions, and set as an origin position of the second belt 432. Thereafter at a step S41, the ninth sample container 100 is clamped in the first measurement unit 2, while the needle (not shown) of the specimen aspirating portion 21 is stuck and passed into the closed lid of the sample container 100. The precedent rack 101 is moved in the forward feeding direction. At a step S42, aspiration of the specimen in the ninth sample container 100 is performed by the specimen aspirating portion 21 in the first measurement unit 2, while the tenth sample container 100 is taken out from the precedent rack 101 by the hand portion 351 of the second measurement unit 3. At this time, the precedent rack 101 is at a stop so that the tenth sample container 100 comes to the second takeout position where the same is taken out by the hand portion 351. Further, the two protruding segments 432*d* are moved to the rack feeding position, and the subsequent rack 101 is fed into the space between the two protruding segments 432*d* of the second belt 432.

At a step S43, the ninth sample container 100 is taken out from the specimen set portion 255*a* by the hand portion 251 and sample preparation, stirring and analysis are performed as to the specimen aspirated by the specimen aspirating portion 21 in the first measurement unit 2. Further, the specimen in the tenth sample container 100 grasped by the hand portion 351 is stirred in the second measurement unit 3, while the precedent rack 101 and the subsequent rack 101 are moved in the forward feeding direction together. At a step S44, the tenth sample container 100 is set on the specimen set portion 355*a* in the second measurement unit 3, and the presence or absence of the first sample container 100 in the subsequent rack 101 is sensed by the presence or absence sensor 45. Thereafter at a step S45, the bar code 100*a* of the tenth sample container 100 is read by the bar code reading portion 356 in the second measurement unit 3, and the presence or absence of the second sample container 100 in the subsequent rack 101 is sensed by the presence or absence sensor 45.

At a step S46, the tenth sample container 100 held on the specimen set portion 355*a* is clamped, while the needle (not shown) of the specimen aspirating portion 31 is stuck and passed into the closed lid of the sample container 100. At this time, the bar code 100*a* of the first in the subsequent rack 101 is read, and the presence or absence of the third sample container 100 is sensed. At a step S47, the ninth sample container 100 is returned from the first measurement unit 2 into the original container storing portion 101*b* of the precedent rack 101, while aspiration of the specimen in the tenth sample container 100 is performed by the specimen aspirating portion 31 in the second measurement unit 3. Further, the subsequent rack 101 is moved in the forward feeding direction. At this time, the bar code 101*a* of the rack 101 is read by the bar code reading portion 44. At a step S48, the tenth sample container 100 is taken out from the specimen set portion 355*a* by the hand portion 351 and sample preparation, stirring and analysis are performed as to the specimen aspirated by the specimen aspirating portion 31 in the second measurement unit 3. The precedent rack 101 is moved in the forward feeding direction. At a step S49, the first sample container 100 is taken out from the subsequent rack 101 by the hand portion 251 of the first measurement unit 2. At this time, the subsequent rack 101 is at a stop on a position where the first sample container 100 corresponds to the first takeout position. Further, the precedent rack 101 retreats on a position in front of the subsequent rack 101 while the first sample container 100 is taken out from the subsequent rack 101, as shown in a state 49 in FIG. 17.

At a step S50, the specimen in the first sample container 100 of the subsequent rack 101 is stirred in the first measurement unit 2, while the precedent rack 101 and the subsequent rack 101 are moved in the backward feeding direction together. In the second measurement unit 3, the measurement as to the specimen in the tenth sample container 100 of the precedent rack 101 is terminated. At a step S51, the first sample container 100 in the subsequent rack 101 is set on the specimen set portion 255a in the first measurement unit 2, while the bar code 100a of the second in the subsequent rack 101 is read, and the presence or absence of the fourth sample container 100 is sensed. At a step S52, the bar code 100a of the first sample container 100 in the subsequent rack 101 is read by the bar code reading portion 256 in the first measurement unit 2. Further, the tenth sample container 100 in the precedent rack 101 is returned from the second measurement unit 3 into the original container storing portion 101b of the precedent rack 101. During this time, the subsequent rack 101 retreats on a position at the back of the precedent rack 101, as shown in a state 52 in FIG. 18.

At a step S53, the first sample container 100 is clamped in the first measurement unit 2, while the needle (not shown) of the specimen aspirating portion 21 is stuck and passed into the closed lid of the sample container 100. The precedent rack 101 and the subsequent rack 101 are moved in the forward feeding direction together. Thereafter at a step S54, aspiration of the specimen in the first sample container 100 is performed by the specimen aspirating portion 21 in the first measurement unit 2, while the second sample container 100 is taken out from the subsequent rack 101 by the hand portion 351 of the second measurement unit 3. At this time, the precedent rack 101 retreats on the rack delivery position, as shown in a state 54 in FIG. 18. At a step S55, the first sample container 100 is taken out from the specimen set portion 255a by the hand portion 251 and sample preparation, stirring and analysis are performed as to the specimen aspirated by the specimen aspirating portion 21 in the first measurement unit 2. Further, the specimen in the second sample container 100 grasped by the hand portion 351 is stirred in the second measurement unit 3, while the subsequent rack 101 is moved in the forward feeding direction.

At a step S56, the second sample container 100 is set on the specimen set portion 355a in the second measurement unit 3, while the bar code 100a of the third in the subsequent rack 101 is read, and the presence or absence of the fifth sample container 100 is sensed. The precedent rack 101 is pressed by the rack delivery portion 46, and moved into the post-analysis rack holding portion 42. At a step S57, the measurement as to the specimen in the first sample container 100 is terminated in the first measurement unit 2, and the bar code 100a of the second sample container 100 is read by the bar code reading portion 356 in the second measurement unit 3. Further, the bar code 100a of the fourth in the subsequent rack 101 is read, and the presence or absence of the sixth sample container 100 is sensed. Further, the two protruding segments 431d of the first belt 431 are moved to a belt retreat place (the back side of the rack transport portion 43), not to hinder movement of the subsequent rack 101 by the second belt 432. Also as to the following sample containers 100, measurement processing is performed in the first measurement unit 2 and the second measurement unit 3 and transport processing of the subsequent rack 101 is performed in the specimen transporter 4, similarly to the above. The drawings are simplified since similar processing is repeated, and it is shown that prescribed processing is performed in each portion at a step S58.

Thereafter at a step S59, aspiration of the specimen in the ninth sample container 100 of the subsequent rack 101 is performed by the specimen aspirating portion 21 in the first measurement unit 2, while the tenth sample container 100 is taken out from the subsequent rack 101 by the hand portion 351 of the second measurement unit 3. At this time, the subsequent rack 101 is at a stop so that the tenth sample container 100 comes to the second takeout position where the same is taken out by the hand portion 351.

At a step S60, the ninth sample container 100 is taken out from the specimen set portion 255a by the hand portion 251 and sample preparation, stirring and analysis are performed as to the specimen aspirated by the specimen aspirating portion 21 in the first measurement unit 2. Further, the specimen in the tenth sample container 100 grasped by the hand portion 351 is stirred in the second measurement unit 3, while the subsequent rack 101 is moved in the forward feeding direction. At a step S61, the tenth sample container 100 is set on the specimen set portion 355a in the second measurement unit 3. Thereafter at a step S62, the measurement as to the specimen in the ninth sample container 100 is terminated in the first measurement unit 2, while the bar code 100a of the tenth sample container 100 is read by the bar code reading portion 356 in the second measurement unit 3. At a step S63, the tenth sample container 100 is clamped in the second measurement unit 3, while the needle (not shown) of the specimen aspirating portion 31 is stuck and passed into the closed lid of the sample container 100. At this time, the subsequent rack 101 is moved in the forward feeding direction.

At a step S64, the ninth sample container 100 is returned from the first measurement unit 2 into the original container storing portion 101b of the subsequent rack 101, while aspiration of the specimen in the tenth sample container 100 is performed by the specimen aspirating portion 31 in the second measurement unit 3. At a step S65, the tenth sample container 100 is taken out from the specimen set portion 355a by the hand portion 351 and sample preparation, stirring and analysis are performed as to the specimen aspirated by the specimen aspirating portion 31 in the second measurement unit 3. The subsequent rack 101 is moved in the forward feeding direction. At a step S66, the measurement as to the specimen in the tenth sample container 100 is terminated in the second measurement unit 3. The tenth sample container 100 is returned from the second measurement unit 3 into the original container storing portion 101b of the subsequent rack 101 at a step S67, while the subsequent rack 101 is moved in the forward feeding direction to the rack delivery position at a step S68. At a step S69, the subsequent rack 101 is pressed by the rack delivery portion 46 and moved into the post-analysis rack holding portion 42, and the operations are terminated. Thus, the series of operations of the first measurement unit 2, the second measurement unit 3 and the specimen transporter 4 of the hemanalysis apparatus 1 according to the first embodiment are performed. While the example in the case where the two racks 101 are transported has been described in the first embodiment, the third and further racks 101 are fed into the rack transport portion 43 similarly to the aforementioned subsequent rack 101 fed into the rack transport portion 43 and processing is performed in each portion similarly to the above in a case where at least three racks 101 are transported.

According to the first embodiment, as hereinabove described, the plurality of measurement units 2 and 3 of mutually identical types, the specimen transporter 4 transporting the specimens to the respective ones of the plurality of measurement units 2 and 3 and the display portion 52, common to the plurality of measurement units 2 and 3, displaying the analytical results generated by analyzing the measurement data are so provided that only the number of the measurement units can be increased or decreased without changing the numbers of the specimen transporter 4 and the display portion 52, whereby the processibility and the price of the hemanalysis apparatus 1 can be easily changed. Thus, the processibility of the hemanalysis apparatus 1 can be easily increased in a large-scale institution by increasing the number of the measurement units while the price of the hemanalysis apparatus 1 can be easily kept low in a small-scale institution by reducing the number of the measurement units, whereby it s possible to flexibly cope in response to the scale of the institution using the hemanalysis apparatus 1. Further, the measurement units of the same type are so employed that the components of the respective measurement units can be rendered common, and the period required for the development and the design of the hemanalysis apparatus 1 can be reduced as a result.

According to the first embodiment, the controller 5 common to the plurality of measurement units 2 and 3 analyzing the measurement data and generating the analytical results is provided while the display portion 52 displaying the analytical results and the control portion 51 transmitting the analytical results to the host computer 6 are provided on the controller 5, whereby it is possible to display the analytical results and to transmit the analytical results to the host computer 6 with one controller 5 also in a case of increasing the number of the measurement units.

According to the first embodiment, the controller 5 is formed to control the operations of the plurality of measurement units 2 and 3 so that it is not necessary to provide the controller 5 every measurement unit, whereby increase in the number of components can be suppressed.

According to the first embodiment, a plurality of identical components are provided on the first measurement unit 2 and the second measurement unit 3 while the identical components are arranged to be symmetrical to each other with respect to the centerline between the two measurement units 2 and 3 so that securement of a working space can be inhibited from being restricted by the other measurement unit when arranging components of each measurement unit having high frequencies of requiring maintenance on an outer direction side, opposite to the side where the two measurement units 2 and 3 are opposed to each other, of each measurement unit where the other measurement unit is not arranged, whereby maintenance operations of the two measurement units 2 and 3 can be easily performed.

According to the first embodiment, the first measurement unit 2 and the second measurement unit 3 are so stored in one housing 10 that both of the first measurement unit 2 and the second measurement unit 3 can be brought into substantially identical environments as to temperatures, humidity etc., whereby the analytical results can be inhibited from being dispersed due to difference in environment.

According to the first embodiment, the specimen transporter 4 is formed to transport the first sample container 100 stored in the rack 101 to the first measurement unit 2 and to transport the second sample container 100 stored in the rack 101 to the second measurement unit 3 so that the plurality of sample containers 100 stored in the rack 101 can be transported to the different measurement units 2 and 3, whereby another sample container 100 stored in the rack 101 can be transported to the other measurement unit without waiting for termination of a specimen measuring operation by one measurement unit. Thus, a plurality of specimens can be efficiently transported to the measurement units.

According to the first embodiment, the specimen transporter 4 is formed to transport the sample containers 100 on the single transport path so that the specimen transporter 4 can be miniaturized as compared with a case of providing a plurality of transport paths, whereby the overall hemanalysis apparatus 1 can be miniaturized.

According to the first embodiment, the display portion 52 is formed to display the measurement unit number of the measurement unit having measured any specimen and the generated analytical results (the number of red blood cells (RBC), the number of platelets (PLT), the quantity of hemoglobin (HBC), the number of white blood cells (WBC) etc.) in association with each other, whereby the analytical results of the specimen can be confirmed through the display portion 52, and by which measurement unit the specimen has been measured can be easily confirmed. In this case, the measurement unit number of the measurement unit having measured the specimen and the generated analytical results (the number of red blood cells (RBC), the number of platelets (PLT), the quantity of hemoglobin (HBC), the number of white blood cells (WBC) etc.) are so displayed on the same screen as shown in FIG. 10 that by which measurement unit the specimen has been measured can be easily confirmed while confirming the analytical results of the specimen.

According to the first embodiment, the control portion 51 is formed to transmit the information of the analytical results (the number of red blood cells (RBC), the number of platelets (PLT), the quantity of hemoglobin (HBC), the number of white blood cells (WBC) etc.) and the measurement unit number information of the measurement unit having measured the specimen to the host computer 6, whereby the analytical results (the number of red blood cells (RBC), the number of platelets (PLT), the quantity of hemoglobin (HBC), the number of white blood cells (WBC) etc.) and the measurement unit number information of the measurement unit having measured the specimen can be confirmed also on the side of the host computer 6.

According to the first embodiment, the first measurement unit 2 and the second measurement unit 3 are formed to generate the measurement data for generating the numbers of red blood cells, the quantities of hemoglobin, the numbers of platelets and the numbers of white blood cells as the analytical results, whereby the hemanalysis apparatus 1 capable of acquiring the numbers of red blood cells, the quantities of hemoglobin, the numbers of platelets and the numbers of white blood cells as the analytical results can be obtained.

According to the first embodiment, the first measurement unit 2 and the second measurement unit 3 are formed to generate the measurement data for generating mutually identical measurement items as the analytical results, whereby the development and the design of the first measurement unit 2 and the second measurement unit 3 can be rendered common. Thus, it is not necessary to develop and design the first measurement unit 2 and the second measurement unit 3 separately from each other, whereby the period required for the development and the design of the measurement units can be reduced.

(Second Embodiment)

Figure 19:
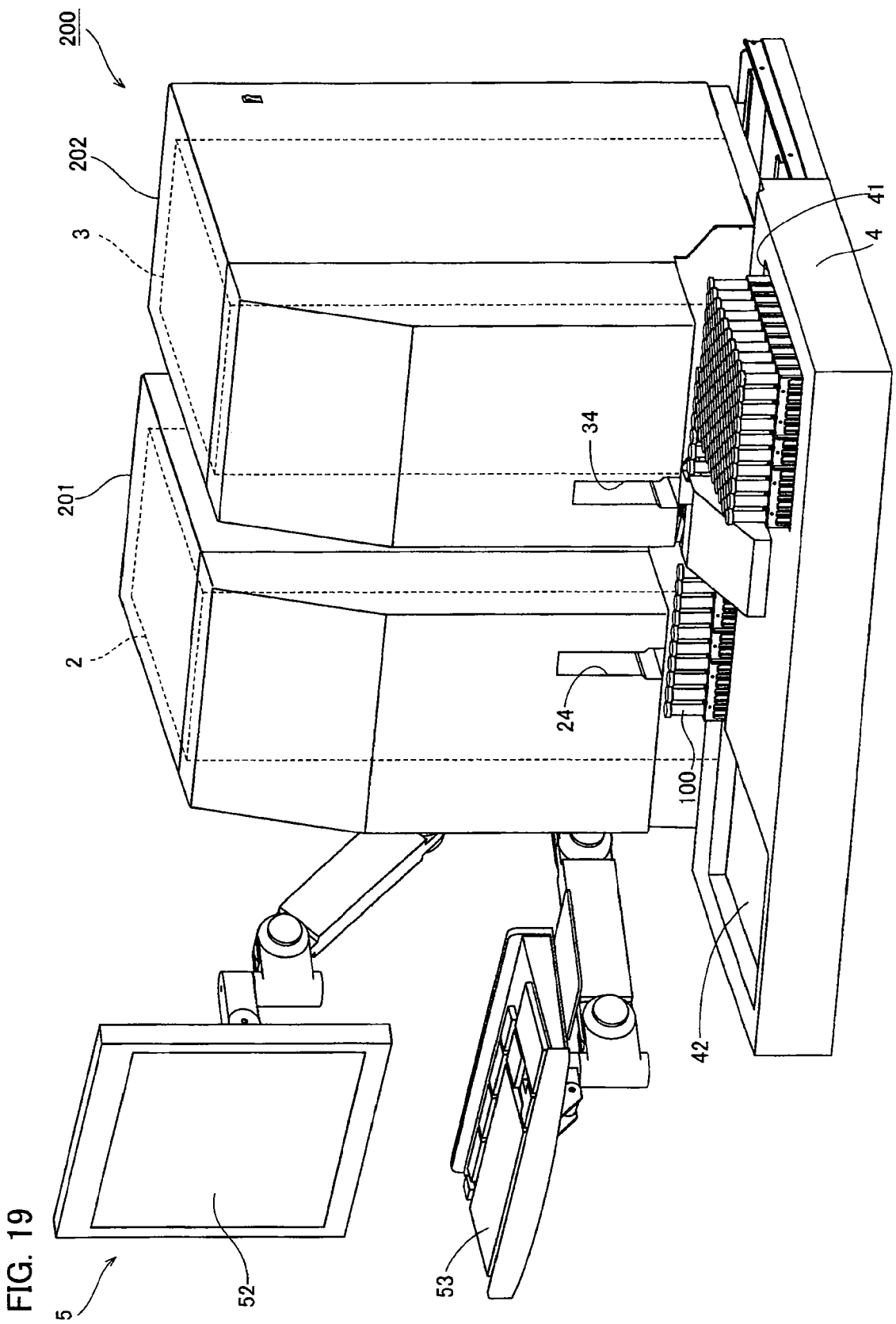
FIG. 19 is a perspective view showing the overall structure of a hemanalysis apparatus according to a second embodiment of the present invention.

Referring to FIG. 19, a hemanalysis apparatus 200 in which a first measurement unit 2 and a second measurement unit 3 are stored in different housings 201 and 202 respectively dissimilarly to the aforementioned first embodiment is described in this second embodiment.

According to the second embodiment, the first measurement unit 2 is stored in the housing 201 and the second measurement unit 3 is stored in the housing 202, as shown in FIG. 19.

The remaining structure of the second embodiment is similar to that of the aforementioned first embodiment.

According to the second embodiment, as hereinabove described, the first measurement unit 2 and the second measurement unit 3 are stored in the different housings 201 and 202, whereby the sizes of the individual housings can be reduced. Thus, the user can easily detach the housings from the measurement units, whereby a burden on the user at a time of performing maintenance and inspection of the measurement units can be reduced.

The remaining effects of the second embodiment are similar to those of the aforementioned first embodiment.

(Third Embodiment)

Figure 20:
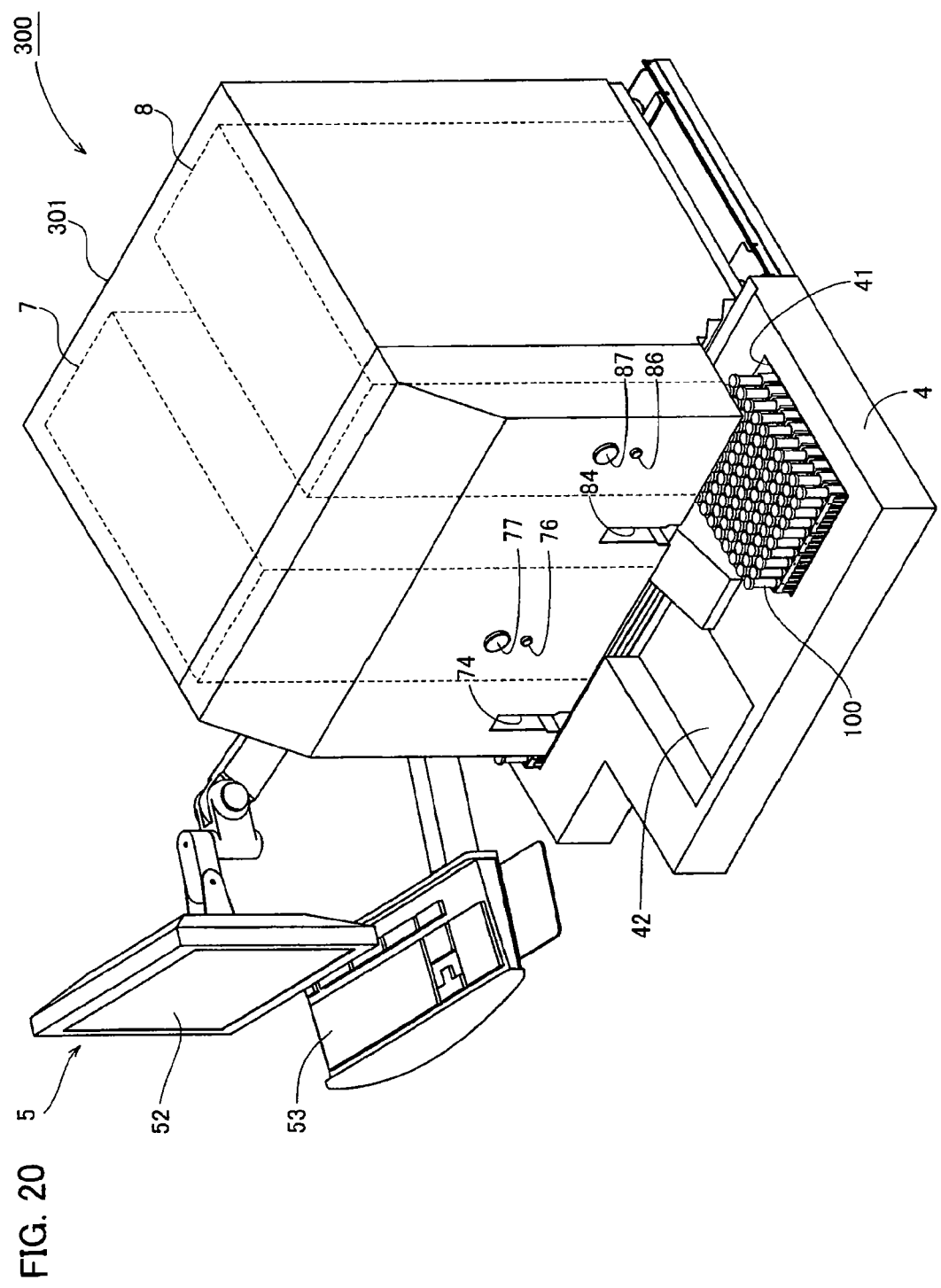
FIG. 20 is a perspective view showing the overall structure of a hemanalysis apparatus according to a third embodiment of the present invention.
Figure 21:
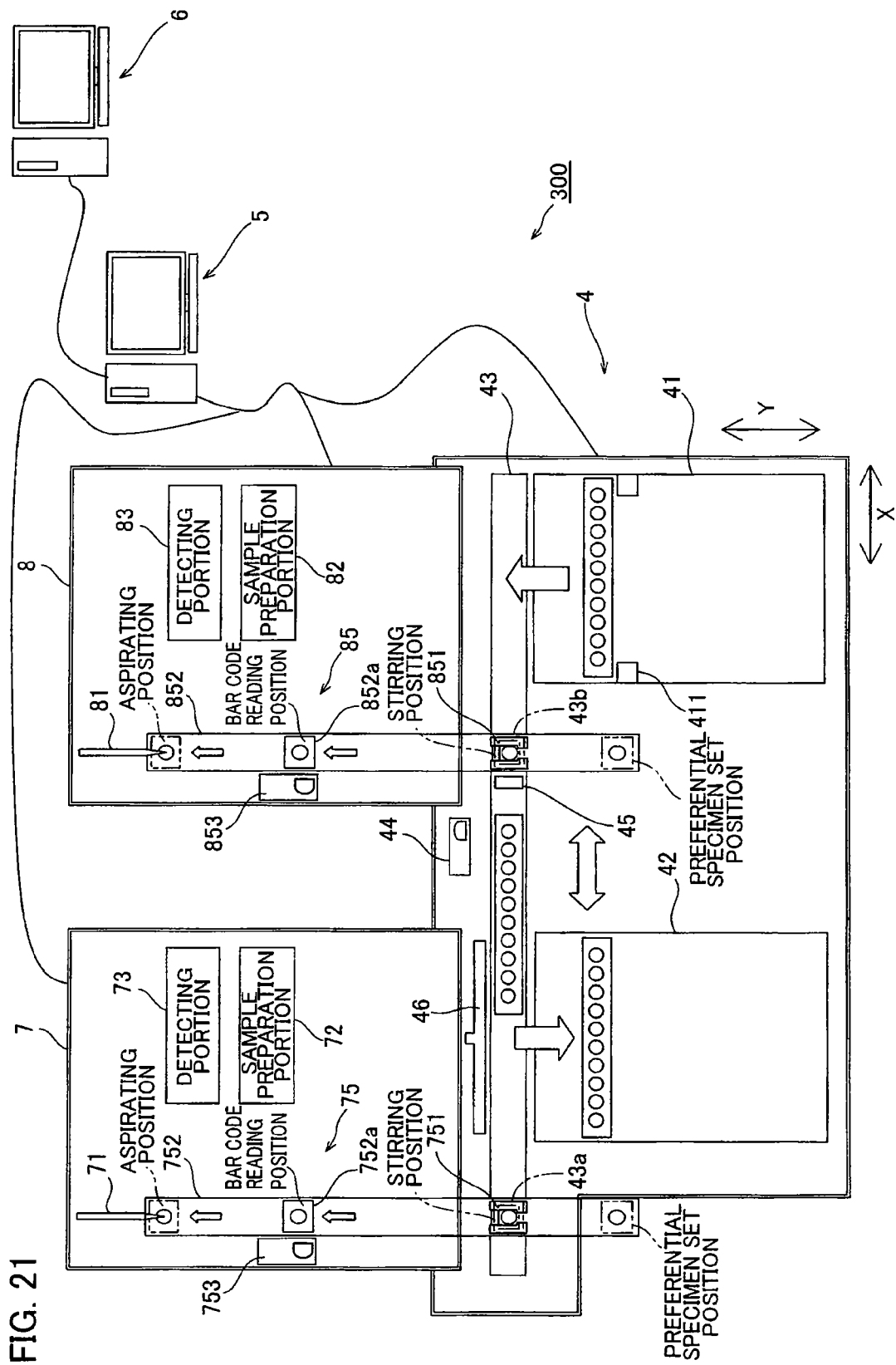
FIG. 21 is a schematic diagram showing measurement units and a specimen transporter of the hemanalysis apparatus according to the third embodiment shown in FIG. 3.

Referring to FIGS. 20 and 21, a hemanalysis apparatus 300 in which a first measurement unit 7 and a second measurement unit 8 are not mirror-shaped but have substantially identical structures dissimilarly to the aforementioned first embodiment is described in this third embodiment.

According to the third embodiment, the hemanalysis apparatus 300 includes two measurement units of the first measurement unit 7 and the second measurement unit 8, stored in one housing 301 (see FIG. 20), having substantially identical structures, a specimen transporter (sampler) 4 arranged on the side of the front surfaces of the first measurement unit 7 and the second measurement unit 8 and a controller 5 consisting of a PC (personal computer) electrically connected to the first measurement unit 7, the second measurement unit 8 and the specimen transporter 4, as shown in FIGS. 20 and 21. The hemanalysis apparatus 300 is connected to a host computer 6 (see FIG. 21) by the controller 5.

The first measurement unit 7 and the second measurement unit 8 are measurement units of substantially identical types (according to the third embodiment, the second measurement unit 8 measures specimens as to identical measurement items by using the same measurement principle as the first measurement unit 7. Further, the second measurement unit 8 performs measurement also as to measurement items not analyzed by the first measurement unit 7), and arranged adjacently to each other. The first measurement unit 7 and the second measurement unit 8 include specimen aspirating portions 71 and 81 aspirating blood forming the specimens from sample containers (test tubes) 100, sample preparation portions 72 and 82 preparing detection samples from the blood aspirated by the specimen aspirating portions 71 and 81 and detecting portions 73 and 83 detecting blood cells in the blood from the detection samples prepared by the specimen preparation portions 72 and 82 respectively. The first measurement unit 7 and the second measurement unit 8 further include incorporation ports 74 and 84 (see FIG. 20) for incorporating the sample containers 100 stored in a rack 101 (see FIG. 4) transported by the specimen transporter 4 thereinto and sample container transport portions 75 and 85 incorporating the sample containers 100 thereinto from the rack 101 and transporting the sample containers 100 to aspirating positions (see FIG. 21) by the specimen aspirating portions 71 and 81 respectively. Specimen set portion switching buttons 76 and 86 and preferential specimen measurement start buttons 77 and 87 are provided on the outer surfaces of the first measurement unit 7 and the second measurement unit 8 respectively.

The sample container transport portions 75 and 85 have hand portions 751 and 851 capable of grasping the sample containers 100 respectively. The sample container transport portions 75 and 85 further have sample container moving portions 752 and 852 holding the sample containers 100 acquired from the rack 101 by the hand portions 751 and 851 on specimen set portions 752a and 852a and horizontally linearly moving the same to the aspirating positions of the specimen aspirating portions 71 and 81 in an arrow Y direction and bar code reading portions 753 and 853 respectively.

The hand portions 751 and 851 are arranged above a transport path for the rack 101 transported by the specimen transporter 4 respectively. Further, the hand portions 751 and 851 are formed to grasp the sample containers 100 stored in the rack 101 in a case where the sample containers 100 are transported to a first providing position 43a for providing specimens to the first measurement unit 7 and a second providing position 43b for providing specimens to the second measurement unit 8 respectively.

The sample container moving portions 752 and 852 are formed to horizontally move the specimen set portions 752a and 852a in the arrow Y direction with power by unshown stepping motors respectively. Thus, the sample container moving portions 752 and 852 can transport the sample containers 100 set on the specimen set portions 752a and 852a to preferential specimen set positions, stirring positions, bar code reading positions and aspirating positions respectively. Further, the sample container moving portions 752 and 852 are formed to pass through positions above the transport path for the rack 101 and to transport the sample containers 100, for intersecting with the transport path for the rack 101 transported in an arrow X direction in plan view. The specimen set portions 752a and 852a are formed to be moved to the preferential specimen set positions (see FIG. 21) in a case where the user presses down the specimen set portion switching buttons 76 and 86 (see FIG. 20). The sample container moving portions 752 and 852 are formed to clamp (fix) the sample containers 100 on the respective aspirating positions by unshown regulating portions.

The specimen set portion switching buttons 76 and 86 are formed to be pressable by the user when performing measurement of preferential specimens.

The preferential specimen measurement start buttons 77 and 87 are formed to be pressable by the user. When the user presses down the preferential specimen measurement start buttons 77 and 87 after setting the preferential specimens on the specimen set portions 752a and 852a, the specimen set portions 752a and 852a on which the preferential specimens are set are incorporated into the measurement units, and measurement is started.

The remaining structure of the third embodiment is similar to that of the aforementioned first embodiment.

According to the third embodiment, as hereinabove described, the first measurement unit 7 and the second measurement unit 8 having substantially identical structures are so provided that it is not necessary to develop and deign the respective measurement units separately from each other, whereby the period required for the development and the design of the measurement units can be reduced. Thus, the period required for the development and the design of the overall hemanalysis apparatus 300 can be reduced.

The remaining effects of the third embodiment are similar to those of the aforementioned first embodiment.

(Fourth Embodiment)

Figure 22:
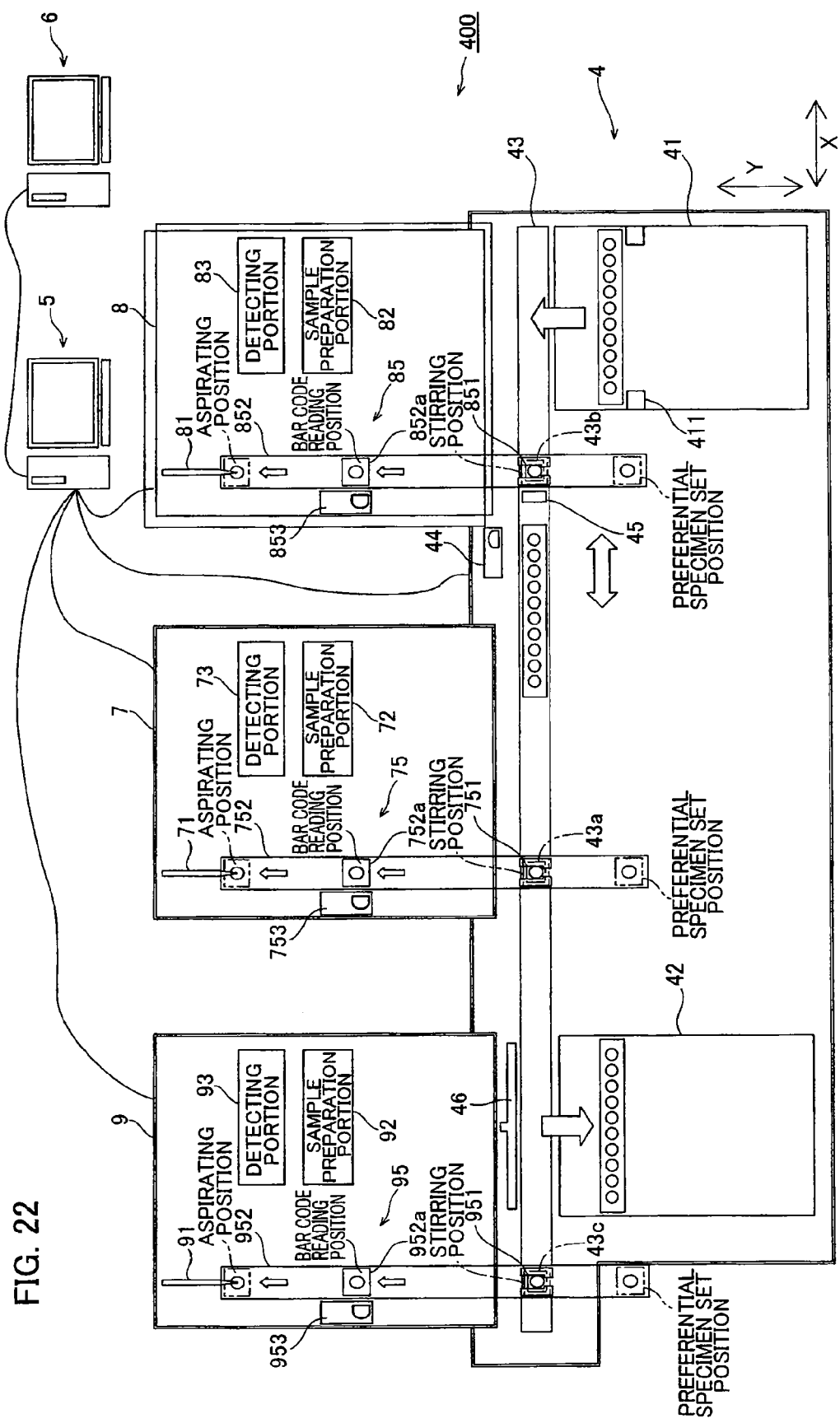
FIG. 22 is a schematic diagram showing measurement units and a specimen transporter of a hemanalysis apparatus according to a fourth embodiment of the present invention.

Referring to FIG. 22, a hemanalysis apparatus 400 including three measurement units of a first measurement unit 7, a second measurement unit 8 and a third measurement unit 9 dissimilarly to the aforementioned third embodiment is described in this fourth embodiment.

According to the fourth embodiment, the hemanalysis apparatus 400 includes the three measurement units of the first measurement unit 7, the second measurement unit 8 and the third measurement unit 9 having substantially identical structures and a specimen transporter (sampler) 4 arranged on the side of the front surfaces of the first measurement unit 7, the second measurement unit 8 and the third measurement unit 9, as shown in FIG. 22.

The first measurement unit 7, the second measurement unit 8 and the third measurement unit 9 are arranged adjacently to each other. The third measurement unit 9 includes a specimen aspirating portion 91 aspirating blood forming specimens from sample containers (test tubes) 100, a sample preparation portion 92 preparing detection samples from the blood aspirated by the specimen aspirating portion 91 and a detecting portion 93 detecting blood cells in the blood from the detection samples prepared by the sample preparation portion 92. The third measurement unit 9 further includes an incorporation port (not shown) for incorporating the sample containers 100 stored in a rack 101 (see FIG. 4) transported by the specimen transporter 4 thereinto and a sample container transport portion 95 incorporating the sample containers 100 thereinto from the rack 101 and transporting the sample containers 100 to an aspirating position by the specimen aspirating portion 91.

The sample container transport portion 95 has a hand portion 951 capable of grasping any sample container 100 transported to a third providing position 43c for providing a specimen to the third measurement unit 9. The sample container transport portion 95 further has a sample container moving portion 952 holding the sample container 100 acquired from the rack 101 by the hand portion 951 on a specimen set portion 952a and horizontally linearly moving the same to the aspirating position of the specimen aspirating portion 91 in an arrow Y direction and a bar code reading portion 953.

The remaining structure of the fourth embodiment is similar to that of the aforementioned third embodiment.

According to the fourth embodiment, as hereinabove described, the three measurement units of the first measurement unit 7, the second measurement unit 8 and the third measurement unit 9 are so provided that processing of specimens can be more rapidly performed as compared with a case where the number of the measurement unit(s) is one or two, whereby it is possible to cope with a large-scale institution in which the number of specimens is large.

The remaining effects of the fourth embodiment are similar to those of the aforementioned third embodiment.

The embodiments disclosed this time must be considered as illustrative in all points and not restrictive. The range of the present invention is shown not by the above description of the embodiments but by the scope of claims for patent, and all modifications within the meaning and range equivalent to the scope of claims for patent are further included.

For Example, while the example of the structure providing the stirring portions on the respective measurement units and stirring the specimens has been shown in each of the aforementioned first to fourth embodiments, the present invention is not restricted to this, but the present invention may be applied to each of analysis apparatuses (such as a biochemical measuring apparatus and a urinalysis apparatus, for example) not stirring specimens. In this case, specimens may be aspirated from sample containers in a state stored in a rack, by moving specimen aspirating portions without providing sample container transport portions.

While the example of singly employing the hemanalysis apparatus has been shown in each of the aforementioned first to fourth embodiments, the present invention is not restricted to this, but the same may be employed as one hemanalysis apparatus among a plurality of hemanalysis apparatuses built into a transport system. Thus, treatability for specimens can be further improved, whereby it is also possible to cope with an institution of a larger scale.

Figure 23:
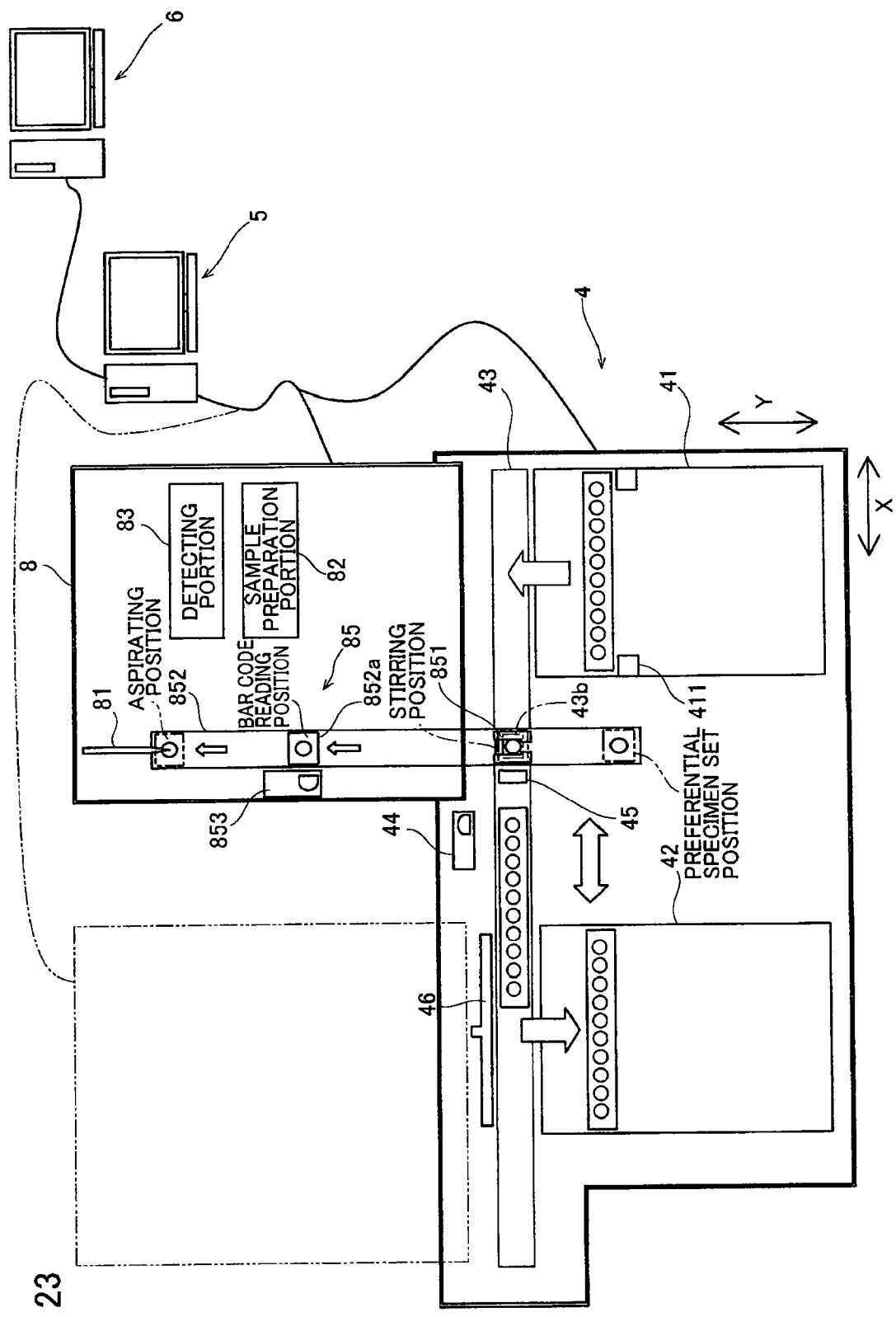
FIG. 23 is a diagram for illustrating a modification of the hemanalysis apparatus according to the first embodiment shown in FIG. 1.

While the hemanalysis apparatus into which two or three measurement units of mutually identical types are built has been shown in each of the aforementioned first to fourth embodiments, the present invention is not restricted to this, but the same may be a hemanalysis apparatus from which another measurement unit other than one measurement unit is detached, as shown in FIG. 23.

While the example of providing one controller controlling the operations of the plurality of measurement units has been shown in each of the aforementioned first to fourth embodiments, the present invention is not restricted to this, but different controllers may be provided for the respective measurement units. Further, these controllers may be built into the respective ones of the first measurement unit, the second measurement unit and the third measurement unit.

While the example of providing the two measurement units of the first measurement unit and the second measurement unit on the hemanalysis apparatus has been shown in each of the aforementioned first to third embodiments, the present invention is not restricted to this, but at least three measurement units may be provided on the hemanalysis apparatus.

While the example of providing the three measurement units of the first measurement unit, the second measurement unit and the third measurement unit on the hemanalysis apparatus has been shown in the aforementioned fourth embodiment, the present invention is not restricted to this, but at least four measurement units may be provided on the hemanalysis apparatus.

The invention claimed is:

1. An analysis apparatus measuring specimens and generating analytical results, comprising:
   a plurality of measurement units configured to generate measurement data by measuring the specimens, wherein the measurement data comprises a quantity of one or more components in the specimens, and wherein a plurality of specimen containers comprising the specimens are stored in alignment in a rack and thereafter are transported;
   a transporter comprising a transport path that consists of a single, straight lane between the plurality of measurement units, the transporter configured to transport the rack on the transport path;
   a controller configured to control the measurement units and the transporter, to generate analytical results by analyzing the measurement data, and to transmit the analytical result to a host computer;
   a display, common to the plurality of measurement units, configured to display the analytical results generated,
   wherein the transporter is configured to transport the rack in two opposing directions on the transport path, wherein the transport path includes takeout positions corresponding to respective measurement units, each of the measurement units is configured to access a specimen container located at the corresponding takeout position and perform a measurement on a specimen in the specimen container,
   each of the plurality of measurement units comprises a hand portion that grasps the sample container,
   the controller is programmed to control the transporter to shuttle the rack between the takeout positions,
   the controller is programmed to control the transporter and the plurality of measurement units to carry out the steps of:
   transporting, using the transporter, the rack storing at least a first specimen container and a second specimen container to the take out position of one measurement unit in the plurality of measurement units,
   removing the first specimen container from the rack at the take out position of the one measurement unit using the corresponding hand portion,
   transporting, using the transporter, the rack to the take out position of another measurement unit in the plurality of measurement units in the state that the first specimen container is removed from the rack, removing the second specimen container from the rack at the take out position of another measurement unit, using the corresponding hand portion, in the state that the first specimen container is removed from the rack, transporting, using the transporter, the rack to the take out position of the one measurement unit in the state that the first specimen container and the second specimen container are removed from the rack, returning the first specimen container in the rack at the take out position of the one measurement unit using the corresponding hand portion, and generating a screen including the analytical results based on the measurement data generated by the plurality of measurement units, wherein the screen is displayed on the display.

2. The analysis apparatus according to claim 1, wherein the controller comprises the display.

3. The analysis apparatus according to claim 2, wherein the controller is configured to control operations of the plurality of measurement units.

4. The analysis apparatus according to claim 1, wherein the plurality of measurement units have substantially identical structures.

5. The analysis apparatus according to claim 1, comprising two measurement units, wherein
the two measurement units include a plurality of identical components, and the identical components are arranged to be symmetrical to each other with respect to a centerline between the two measurement units.

6. The analysis apparatus according to claim 1, wherein the plurality of measurement units are stored in one housing.

7. The analysis apparatus according to claim 1, wherein
the transporter is configured to transport a first specimen container, stored in a rack, storing a first specimen to one measurement unit in the plurality of measurement units and to transport a second specimen container, stored in said rack, storing a second specimen to another measurement unit in the plurality of measurement units.

8. The analysis apparatus according to claim 1, wherein
the transporter is configured to transport the specimen containers on the single transport path.

9. The analysis apparatus according to claim 1, wherein
the controller is configured to transmit the analytical results and information indicating the measurement units having measured the specimens to the host computer.

10. The analysis apparatus according to claim 1, wherein
the specimens are blood, and
the plurality of measurement units are configured to measure the numbers of blood cells in the blood.

11. The analysis apparatus according to claim 10, wherein
the plurality of measurement units are configured to generate measurement data for generating at least the numbers of red blood cells, the quantities of hemoglobin, the numbers of platelets and the numbers of white blood cells as the analytical results.

12. The analysis apparatus according to claim 1, wherein
the plurality of measurement units are configured to generate measurement data for generating mutually identical measurement items as the analytical results.

* * * * *